(12) United States Patent
Pi et al.

(10) Patent No.: US 7,060,964 B1
(45) Date of Patent: Jun. 13, 2006

(54) REFLECTION-MODE FIBER SENSING DEVICES

(75) Inventors: Bo Pi, Carlsbad, CA (US); Wei-Cheng Wilson Lin, Carlsbad, CA (US); Zhihao Chen, Carlsbad, CA (US)

(73) Assignee: IFOS, Inc., Santa Clara, CA (US)

( * ) Notice: Subject to any disclaimer, the term of this patent is extended or adjusted under 35 U.S.C. 154(b) by 0 days.

(21) Appl. No.: 10/785,718

(22) Filed: Feb. 23, 2004

Related U.S. Application Data

(63) Continuation-in-part of application No. 10/714,503, filed on Nov. 12, 2003.

(60) Provisional application No. 60/448,940, filed on Feb. 21, 2003, provisional application No. 60/431,026, filed on Dec. 4, 2002, provisional application No. 60/425,991, filed on Nov. 12, 2002.

(51) Int. Cl.
   *G02B 6/26* (2006.01)

(52) U.S. Cl. ............... 250/227.14; 385/30; 385/15; 385/18

(58) Field of Classification Search ............ 385/30, 385/12, 37, 15, 18, 140, 10; 250/227.14, 250/227.18
See application file for complete search history.

(56) References Cited

U.S. PATENT DOCUMENTS

| 6,011,881 | A  | * | 1/2000  | Moslehi   | 385/10  |
|-----------|----|---|---------|-----------|---------|
| 6,490,391 | B1 |   | 12/2002 | Zhao et al. | 385/30  |
| 6,501,875 | B1 |   | 12/2002 | Zhao et al. | 385/30  |
| 6,516,114 | B1 |   | 2/2003  | Zhao et al. | 385/30  |
| 6,542,663 | B1 |   | 4/2003  | Zhao et al. | 385/30  |
| 6,549,713 | B1 |   | 4/2003  | Pi et al.   | 385/137 |
| 6,556,746 | B1 |   | 4/2003  | Zhao et al. | 385/30  |
| 6,571,035 | B1 |   | 5/2003  | Pi et al.   | 385/30  |
| 6,597,833 | B1 |   | 7/2003  | Pi et al.   | 385/30  |
| 6,621,951 | B1 |   | 9/2003  | Zhao et al. | 385/30  |
| 6,621,952 | B1 |   | 9/2003  | Pi et al.   | 385/30  |
| 6,625,349 | B1 |   | 9/2003  | Zhao et al. | 385/30  |

OTHER PUBLICATIONS

Ramos, et al.; Oblique-Tip Fiber-Optic Sensors for Multiphase Fluid Discrimination; Journal of Lightwave Technology, vol. 17, No. 8, Aug. 1999.

* cited by examiner

*Primary Examiner*—Thanh X. Luu
*Assistant Examiner*—Tony Ko
(74) *Attorney, Agent, or Firm*—Jay A Chesavage

(57) ABSTRACT

Fiber sensors formed on side-polished fiber coupling ports based on evanescent coupling are described. Such sensors may be configured to measure various materials and may be used to form multi-phase sensing devices. A Bragg grating may be implemented in such sensors to form reflective fiber sensors.

13 Claims, 21 Drawing Sheets

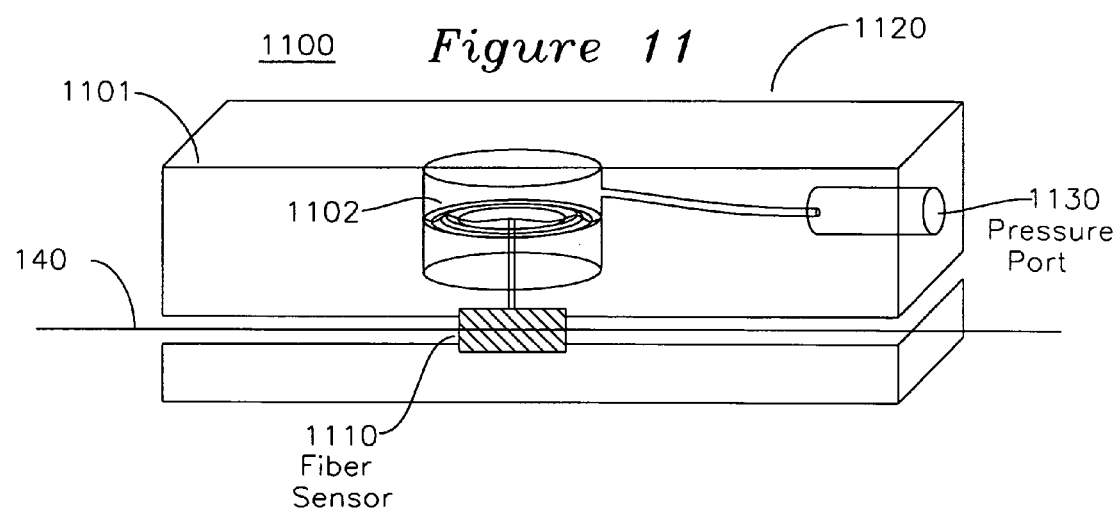

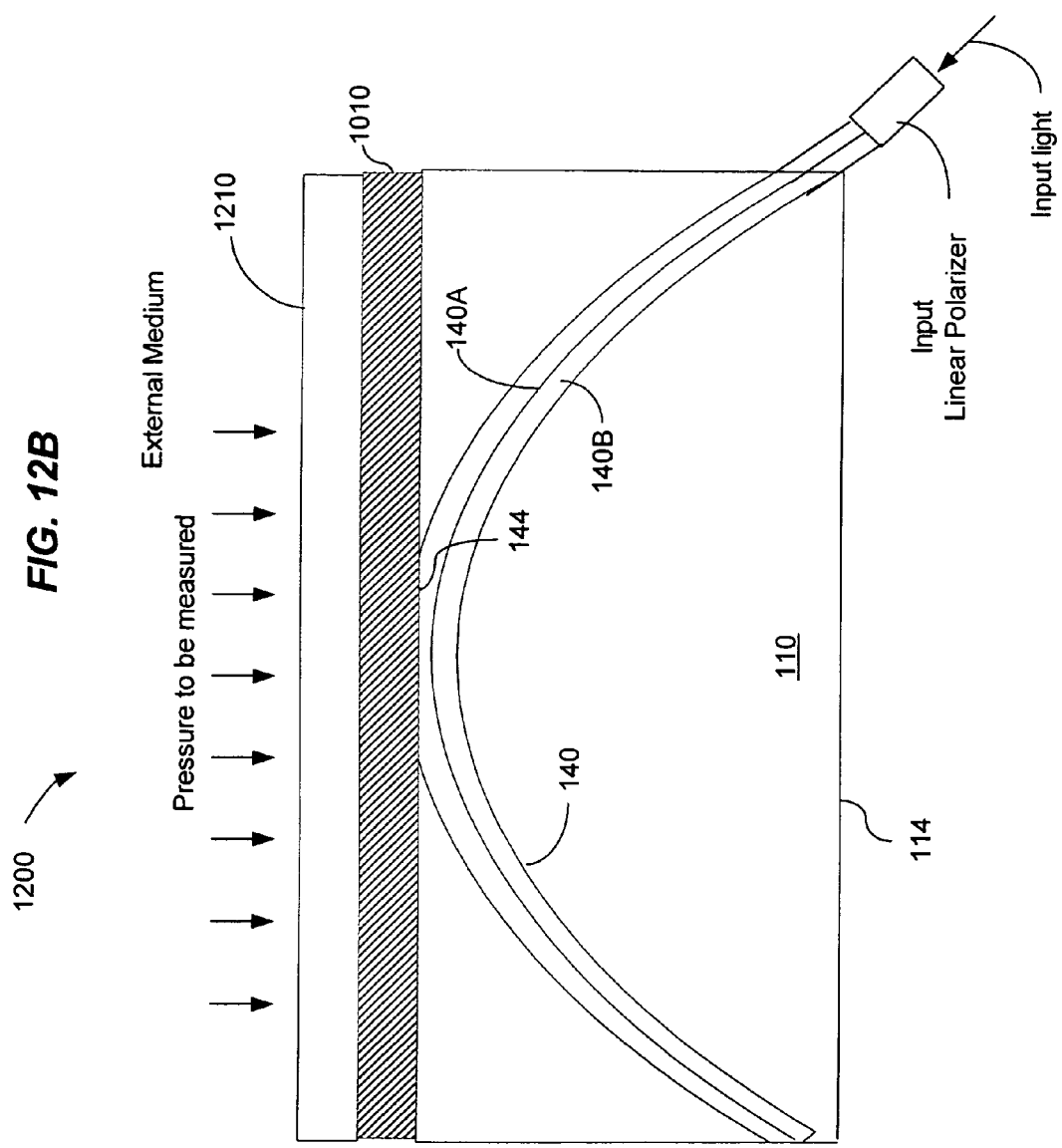

Computed Transverse Mode Profile (m=0, $n_{eff}$=1.455242, 2.067e−9)

REFLECTION-MODE FIBER SENSING DEVICES

This application claims the benefit of U.S. Provisional Application No. 60/448,940 filed Feb. 21, 2003.

This application is also a continuation-in-part application of a co-pending U.S. patent application Ser. No. 10/714,503 filed on Nov. 12, 2003 which further claims the benefits of U.S. Provisional Application Nos. 60/425,991 filed Nov. 12, 2002, 60/431,026 filed Dec. 4, 2002.

The entire disclosures of the above patent applications are incorporated herein by reference as part of this application.

BACKGROUND

This application relates to optical sensing devices based on evanescent optical coupling through a side-polished surface in an optical waveguide such as fibers and planar waveguides.

Optical fibers can be used to transmit or process light in a variety of applications, including delivering light to or receiving light from integrated optical components or devices formed on substrates, transmitting information channels in wavelength-division multiplexed optical communication devices and systems, forming fiber optic switch matrix devices or fiber array to array connector, and producing optical gain for optical amplification or laser oscillation. Optical fibers essentially operate as "light pipes" to confine light within the fiber boundary and transfer light from one point to another.

A typical fiber may be simplified as a fiber core and a cladding layer surrounding the fiber core. The refractive index of the fiber core is higher than that of the fiber cladding to confine the light. Light rays that are coupled into the fiber core within a maximum angle with respect to the axis of the fiber core are totally reflected at the interface of the fiber core and the cladding. This total internal reflection provides a mechanism to spatially confine the optical energy of the light rays in one or more selected fiber modes to guide the optical energy along the fiber core. Similarly, optical waveguides on substrates such as planar and other waveguides may also operate as light pipes to confine and transfer port light and may be used in integrated optical devices where optical elements, opto-electronic elements, or MEMS elements are integrated on one or more substrates.

The guided optical energy in the fiber or waveguide, however, is not completely confined within the core of the fiber or waveguide. In a fiber, for example, a portion of the optical energy can "leak" through the interface between the fiber core and the cladding via an evanescent field that essentially decays exponentially with the distance from the core-cladding interface. The distance for a decay in the electric field of the guided light is less than or on the order of one wavelength of the guided optical energy. This evanescent leakage may be used to couple optical energy into or out of the fiber core, or alternatively, to perturb the guided optical energy in the fiber core.

SUMMARY

This application describes examples of fiber sensing devices based on evanescent optical coupling. According to one implementation, a fiber is provided to include a side surface formed on fiber cladding where an evanescent field of guided light in the fiber exists. A waveguide is formed over the side surface and is exposed to an external medium to cause a change at the side surface. A wavelength shift in a spectral peak in optical loss of light guided in the fiber is monitored and information about the external medium is extracted based on the wavelength shift.

In another implementation, a fiber sensing device includes a fiber having a side surface formed on fiber cladding within a reach of an evanescent field of guided light in the fiber. In addition, a waveguide is formed over the side surface and has a refractive index greater than an effective refractive index of the fiber. An optical detector is used to receive guided light in the fiber transmitting through a section with the side surface to produce a detector output to represent a measurement of an external medium in contact with the waveguide.

In the above and other fiber sensing devices based on the evanescent coupling at a side surface, a reflective Bragg grating may be formed at or above the side surface to reflect light back so that reflected light can be measured to extract information about the external medium. Two or more reflective fiber sensors may be formed in a single fiber and the reflected signals from the sensors may be distinguished by the timings of arrival at an optical detector.

These and other implementations are described in greater detail in the drawings, the detailed description, and the claims.

BRIEF DESCRIPTION OF THE DRAWINGS

FIG. 11 shows an exemplary device configuration for a pressure sensing device shown in FIG. 10A.

FIGS. 12A and 12B show the sensing device in FIG. 12 with a linear polarizer in the input under two different configurations.

DETAILED DESCRIPTION

The optical sensing devices under various implementations of this application are in part based on the recognition that the power of the evanescent light of the guided light in the fiber or waveguide may be used to represent the power of the guided light. A small amount of the evanescent light may be accessed from a side-polished fiber or waveguide and then may be coupled into an optical detector. When the percentage of the received evanescent light out of the total guide light in the fiber is known, the power of the detected evanescent light can be used to measure the absolute power within the fiber. In particular, the location at which the evanescent coupling may be selected so that only a desired small percentage of the guided light, e.g., a few percent or less (i.e., a fraction of one percent), is coupled into the optical detector. Such a device essentially does not change the original polarization state of the guided light when the fiber is the polarization-maintaining type.

Notably, the evanescent coupling is sensitive to the boundary conditions at or near the side-polished coupling port of the fiber or waveguide. For example, if the environment around the side-polished coupling port changes the boundary conditions for the evanescent coupling, the evanescent coupling can change accordingly. This change can be reflected in the remaining guided light in the fiber or waveguide. Hence, a measurement of this change in the remaining guided light in the fiber or waveguide may be calibrated and used to measure the change in the environment. Therefore, this evanescent coupling mechanism may be used to provide optical sensing of the environment. As described in the examples in this application, this evanescent coupling mechanism may provide optical sensing in real time for a range of sensing applications, including measurements of temperature, pressure, presence of selected materials, and others.

The fiber in the sensing devices of this application may be integrated on a substrate. One or more fibers may be integrated on or engaged to the substrate fabricated with one or more grooves. One portion of the cladding of each fiber is removed and polished to form a fiber coupling port as a part of the sensor. In general, the polished surface on the fiber cladding is sufficiently close to the fiber core so that optical energy can be coupled via evanescent fields out of the fiber core for optical monitoring. Two or more such fiber coupling ports may be formed at different positions in each fiber when needed. The following sections first describe the basic structures for integrating fibers onto substrates for forming side-polished fiber coupling ports based on evanescent coupling. Exemplary implementations of fiber sensors based on such structures are then described in detail.

Figure 1:
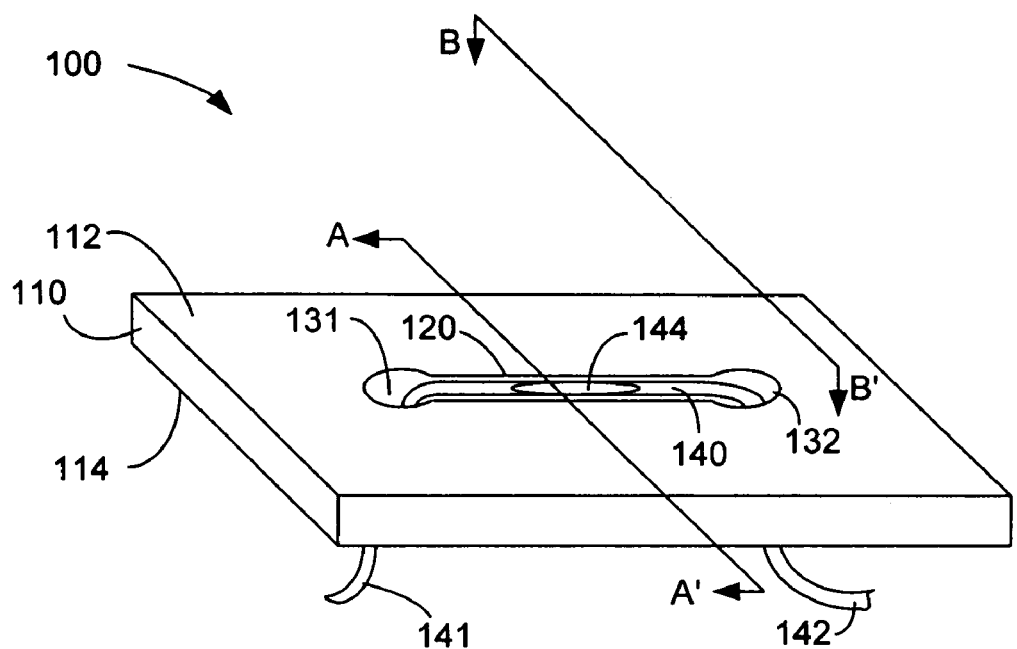
FIG. 1 shows one exemplary implementation of a fiber device that integrates or engages a fiber to a substrate with a groove for positioning the fiber and openings for holding the fiber.
Figure 2A:
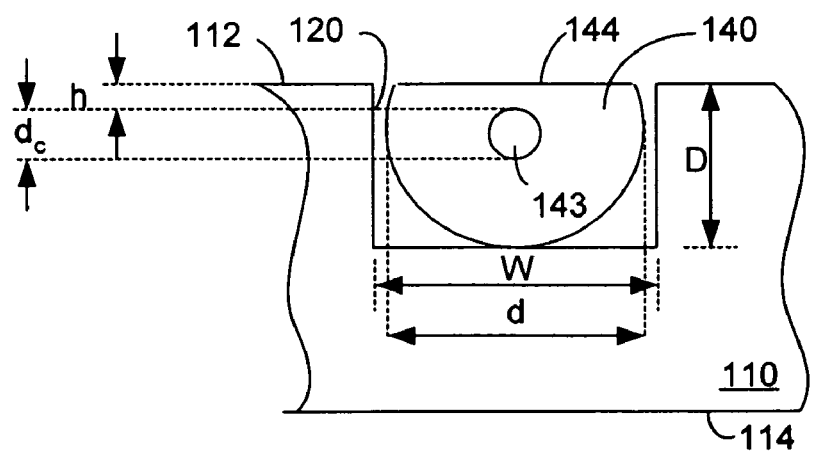
FIGS. 2A and 2B show a cross sectional view of the device in FIG. 1 along the direction AA' and a side view of the device in FIG. 1 along the direction BB', respectively.
Figure 2B:
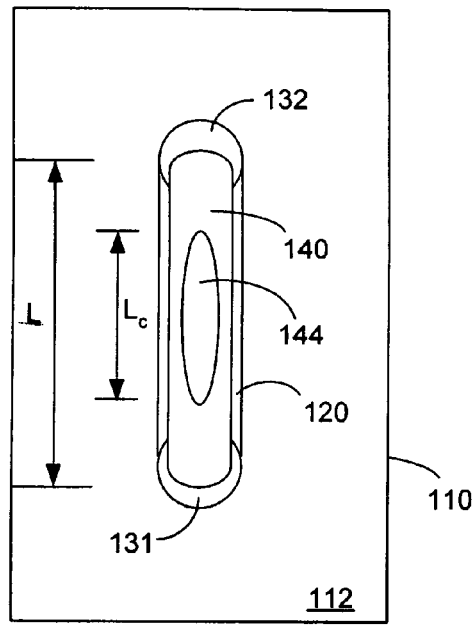

FIG. 1 shows one exemplary implementation of a fiber device 100 where a fiber 140 is integrated or engaged to a substrate 110. The fiber device 100 may be used as a building block to construct a variety of fiber devices, including but not limited to, fiber optical monitors, fiber couplers, fiber attenuators, fiber modulators, fiber beam splitters, optical fiber switches, and fiber frequency-division multiplexers. FIGS. 2A and 2B show additional details of the fiber device 100.

The substrate 110 may be formed of various materials, such as semiconductors, insulators including dielectric materials (e.g., a glass, a quartz, a crystal, etc), metallic materials, or any other solid-state materials that can be processed to form the device features such as grooves and through holes disclosed herein. Two parallel and opposing substrate surfaces, 112 and 114, are generally flat and may be polished. An elongated groove 120 is formed in the substrate 110 on the surface 112 and is essentially a recess from the surface 112. The groove 120 may be fabricated by removing a portion of the material from the substrate 110 through etching or other processes.

Figure 2C:
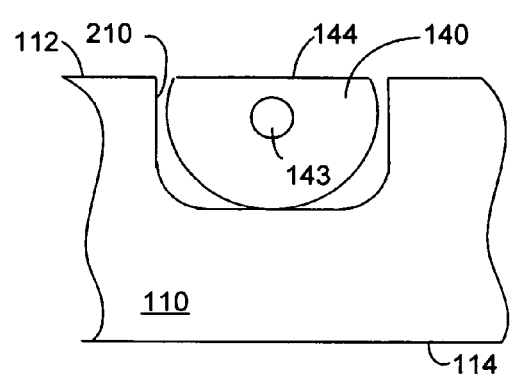
FIGS. 2C and 2D show examples of two different cross sections for grooves shown in FIG. 1.
Figure 2D:
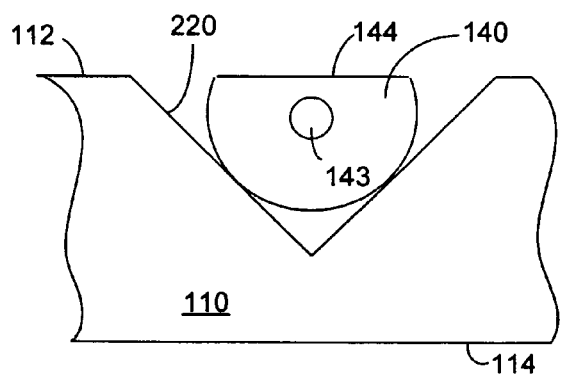

The geometry of the groove 120 is generally elongated along a straight line as illustrated or along a curved line. Unless otherwise indicated, the following description will use straight-line grooves as examples. Some exemplary implementations are described with specific reference to groove with V-shaped cross sections as shown by the groove 220 in FIG. 2D. The cross sections are generally not so limited and may also be other shapes as well, including rectangular as shown in FIG. 2A, U-shaped as shown by the groove 210 in FIG. 2C, a circularly shape or other suitable shapes. Unless specifically indicated otherwise, the techniques, structures, and applications disclosed in this application are generally applicable to grooves of different shapes.

Figure 2E:
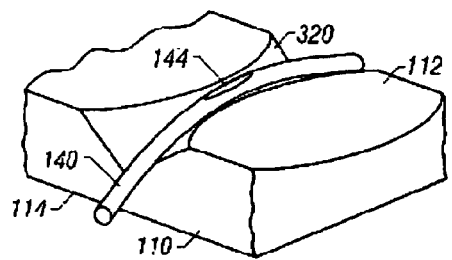
FIG. 2E shows one example of a V groove with varying depth and width.

The width, W, of the groove 120 is generally greater than the diameter, d, of the fiber 140 and may either remain a constant or vary spatially along the groove 120, e.g., increasing from the center towards the two ends as illustrated in the V groove 220 in FIG. 2E. The length, L, of the groove 120 may vary from one grove to another and can be determined based on specific requirements of applications. The depth D of the groove 120 may be a constant or may vary along the groove 120, e.g., increasing from the center towards the two ends as shown in FIG. 2E. In general, at least a portion of the groove 120 has a depth D to expose a portion of the fiber cladding of the fiber 140 above the surface 112 while still keeping the fiber core below the surface 112. Sometimes, the depth D of the groove 120 may also be selected to expose the fiber core. Other portions of the groove 120 may have a different depth so that the fiber can be placed within the groove 120 under the substrate surface 112. Depending on the geometry of the groove 120 (e.g., the apex angle of a V-shaped groove), the depth D of the entire groove 120 may be greater than fiber diameter d. For a groove with a rectangular cross section as shown in FIG. 2A, at least a portion of the groove 120 has a depth D less than the fiber diameter d but greater than the sum of the fiber radius $r=d/2$ and radius of the fiber core $r_c=d_c/2$. This portion of the groove 120 exposes partial fiber cladding of the fiber 140 above the surface 112 while still keeping the fiber core below the surface 112. Other portions of the groove 120 may have a depth that is at least the fiber diameter d so that the fiber can be essentially placed in the groove 120 below the surface 112. However, in certain applications, the depth D of the entire groove 120 may be greater than fiber diameter d to avoid evanescent coupling of a guided mode. Unless otherwise indicated, the following description will assume that at least a portion of a groove 120 to expose a portion of the fiber cladding above the surface 112 and adjacent portions sufficiently deep to keep the fiber below the surface 112. In case of the rectangular groove 120, the central portion of the groove 120 may have a depth D less than d but greater than $(d+d_c)/2$ while the portions on either sides of the central portion may have a depth equal to or greater than the fiber diameter d.

Notably, the fiber device 100 includes two openings 131 and 132 that are respectively formed at the two ends of the groove 120 and penetrate through the substrate 110. Hence, the openings 131 and 132 are through holes extending between the two surfaces 112 and provide access from one surface (112 or 114) to another. The spacing between the openings 131 and 132 essentially determines the length L of the groove 120. The aperture of the openings 131 and 132 should be sufficiently large to receive the fiber 140, e.g., with a diameter greater than the diameter of the fiber 140. The shape of the holes 131 and 132 may generally be in any suitable geometry.

A portion of the fiber 140 is placed in the groove 120 near the surface 112. The remaining portions 141, 142 of the fiber 140 on both sides of the portion in the groove 120 are respectively fed through the first and second openings 131, 132 to the other side 114 of the substrate 110. After being placed in the substrate 110 as shown in FIG. 1, the fiber 140 may be slightly pulled by moving the fiber portions 141 and 142 in opposite directions so that the portion of the fiber 140 in the groove 120 is in substantially full contact with the groove 120.

Since a portion of the groove 120 has a depth D less than the fiber diameter d, the cladding of the fiber 140 in this portion protrudes out of the surface 112. The fiber core in this portion of the fiber is generally kept under the surface 112. For example, the cladding of a central portion of the fiber 140 between the holes 131 and 132 may be exposed. This protruded or exposed cladding is then removed and polished to form a flat surface 144 of a length $L_c$ that is above the fiber core 143 and is substantially coplanar with the surface 112 of the substrate 110 as illustrated in FIG. 2B. When the spacing, h, between the flat surface 144 and the fiber core 143 is sufficiently small (e.g., on the order of or less than one wavelength of optical energy), the flat surface 144 can be used to couple optical energy into or out of the fiber core 144 is through the evanescent fields outside the fiber core. Hence, the length, $L_c$, of the flat surface 144 approximately represents the optical coupling length for the fiber device 100. This coupling surface 144 may also be non-flat, e.g., curved to a certain extent, as long as it can transmit evanescent signals.

Alternatively, only one through hole 132 in the substrate 110 may be needed to engage the fiber 140 to form the fiber module for coupling with a waveguide module. As shown in the design 301 in FIG. 3A, the groove 120 may extend to one end side 310 of the substrate 110 so that one end 141 of the fiber 140 leaves the groove 120 without going through a through hole. In addition, FIG. 3B shows a conventional design 302 in which the groove 120 may extend to two opposing end sides 310 and 330 of the substrate 110 so that the fiber 140 is engaged to the groove 120 without relying on any through holes.

Figure 3A:
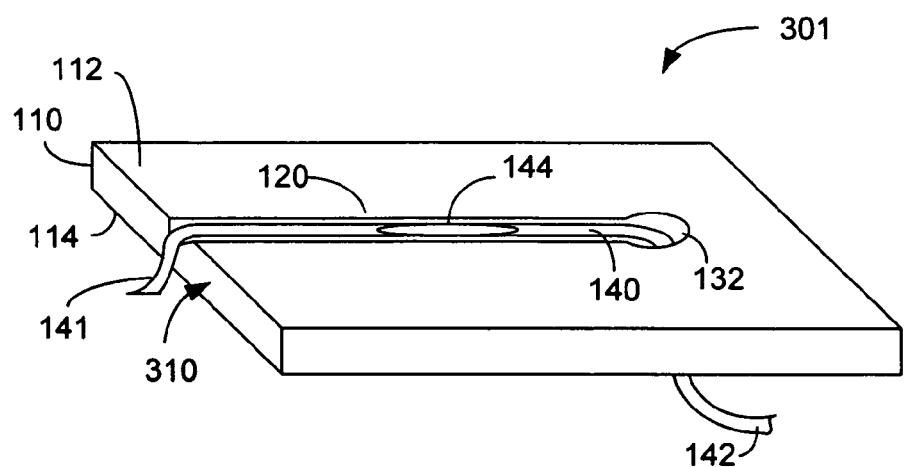
FIG. 3A shows a design to engage a fiber on to a substrate by using an elongated groove with a single through hole, where a portion of the fiber cladding is removed and polished to form a side-polished evanescent coupling port.
Figure 3B:
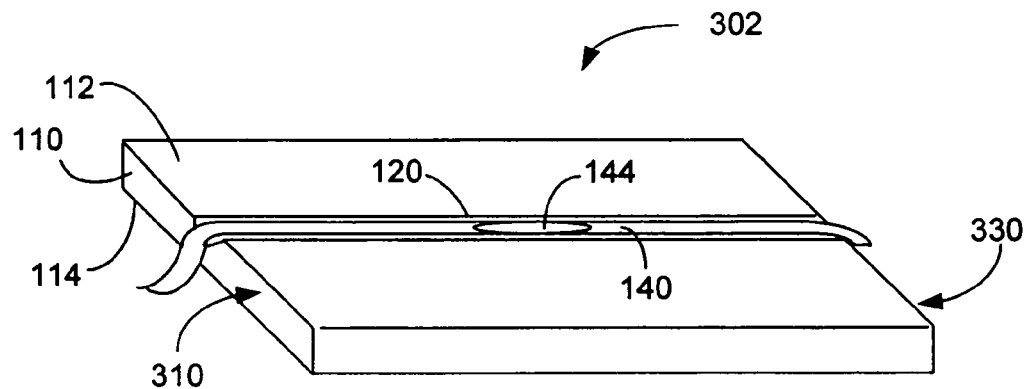
FIG. 3B shows another way of engaging a fiber onto a substrate without using through holes shown in FIG. 1, where a portion of the fiber cladding is removed and polished to form a side-polished evanescent coupling port.
Figure 4:
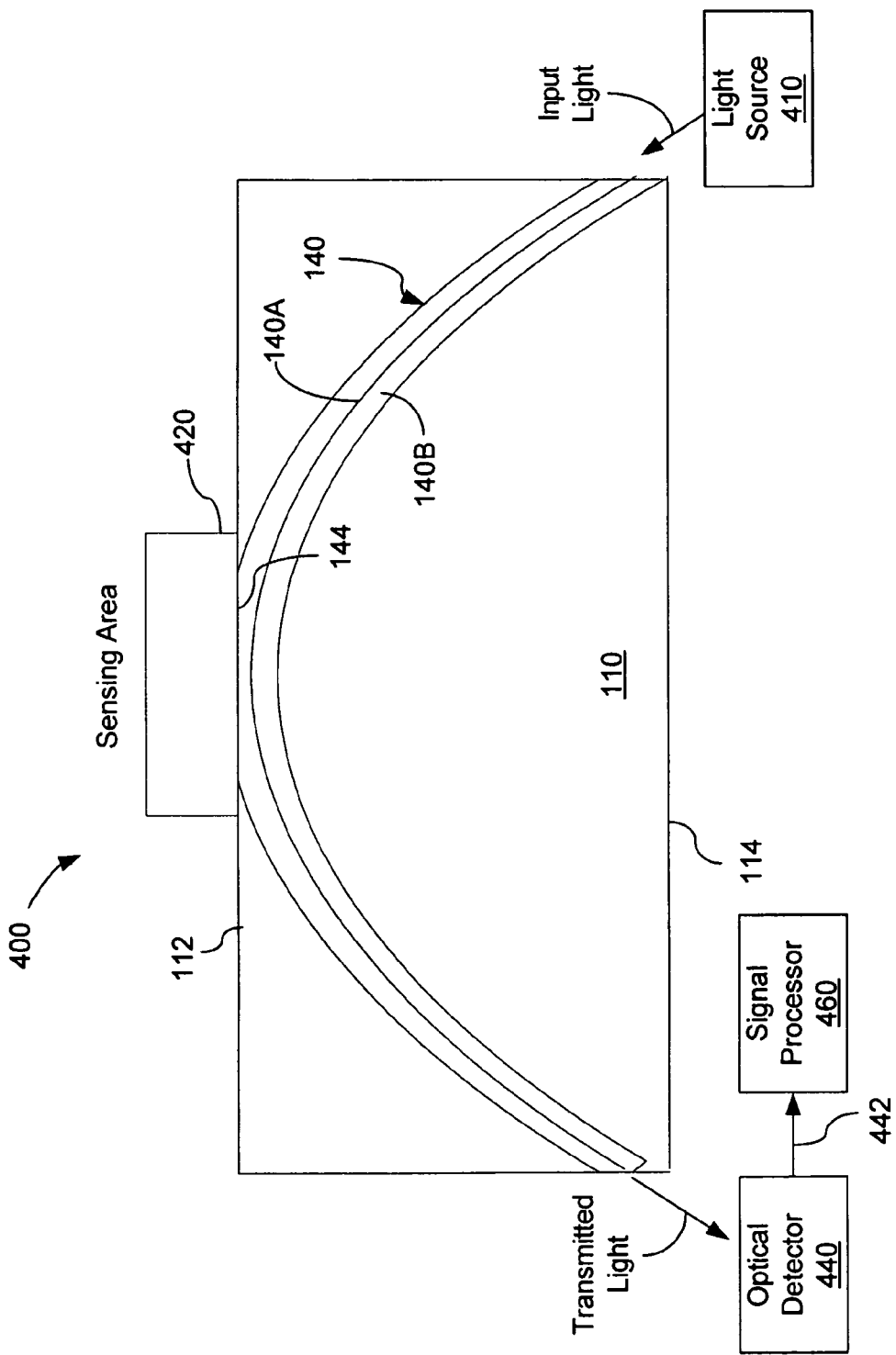
FIG. 4 shows one exemplary fiber sensing device formed over a side-polished fiber.

Notably, the through holes in the substrate 110 shown in FIGS. 1 and 3A, may be used to engage a single fiber on both sides of a substrate to form two or more side-polished coupling ports for evanescent coupling. For example, two grooves may be formed on opposite sides of the substrate 110 to share a common through hole at ends. A fiber may be threaded through the substrate 110 to have one fiber portion in the groove on one side and another fiber portion in the groove on the opposite side of the substrate 110. Hence, fiber coupling ports may be formed in the same fiber on both sides of the substrate 110. This structure may be use to construct a variety of fiber devices, including stacking two substrates to provide optical coupling from a fiber in one substrate to another fiber in another substrate. The fabrication of this double-sided fiber structure may be implemented by polishing the substrate and the fiber on both sides as described FIG. 4 shows one exemplary implementation of a fiber sensing device 400. A fiber 140 with a core 140A and a cladding 140B has one portion whose cladding is partially removed to form a surface 144. The surface 144 is within the extent of the evanescent field of the guided light in the fiber core 140A. The surface 144 is polished to operate as the fiber coupling port. The amount of evanescent light at the surface 144 may be set at a desired percentage of the total guide ling in the fiber 140 by controlling the distance between the fiber core 140A and the surface 144 during the fabrication phase. The evanescent light decays in magnitude exponentially with the distance. Hence, the closer the surface 144 to the fiber core 144A, the higher the percentage of the evanescent light being coupled out of the fiber.

In the device 400, the substrate 110 is shown to operate as a fiber support that holds the fiber 140. The substrate 110 has two opposing surfaces 112 and 114. A depth-varying groove 120 may be formed on the surface 112 of the substrate 110. When the fiber 140 is placed in the groove 120, the cladding of the fiber portion where the surface 144 is formed protrudes above the surface 112. The protruded cladding is then removed to form the surface 144 which is approximately coplanar with the surface 112. Other portions of the fiber 140 in the groove 120 stay under the surface 112. As described above, different ways may be used to engage the fiber 140 to the substrate 110 to form the fiber coupling port 144 for evanescent coupling.

Notably, a high-index transparent overlay layer 420 is formed over the surface 144. The overlay 420 may have an index higher than the effective index that of the fiber 140 to assist extraction of the evanescent light out of the guide mode of the fiber 140. The property of the overlay layer 420, such as the index, the thickness, the order of the waveguide of the overlay 420, its mechanical properties including Young's modulus and Poisson ratio may be selected to meet the specific sensing operations. More details on this aspect of the sensors are described at later sections of this application. The top of the overlay layer 420 is exposed to the external medium as the sensing area for the sensing device 400.

The fiber 140 generally may be any fiber, including single-mode fibers, multi-mode fibers, and birefringent fibers. In particular, the fiber 140 may be a polarization maintaining (PM) fiber to preserve the polarization state of light to be transmitted.

A light source 410 such as a laser diode or other suitable light-emitting device is provided to supply input light as the probe light to the sensor 400. The fiber sensing device 400 further includes an optical detector 440 that is optically coupled to receive a portion or the entirety of the transmitted light in the fiber 140 that passes through the fiber section with the port 144 and the overlay 144. The received transmitted light is converted into a detector signal 442. A signal processor 460 is used to process the detector signal 442 to extract the desired information about the parameter measured by the sensing device 400, such as the pressure or temperature at the waveguide 420 and the port 144. The processor 460 has the processing logic that correlates a change in the evanescent coupling, such as a wavelength shift for the maximum evanescent coupling, at the port 144 in the transmitted light received by the detector 440 and the parameter to be measured.

Figure 5:
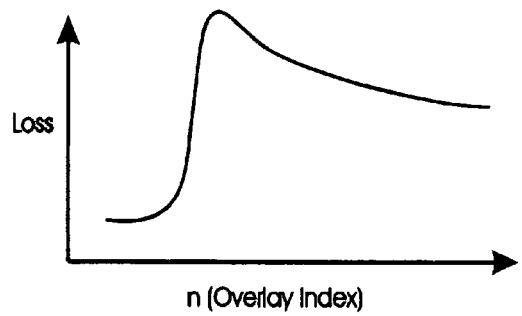
FIGS. 5 and 6 illustrate optical properties of the device in FIG. 4.

FIG. 5 shows the optical loss in the guided light through the side-polished coupling port 144 and the overlay layer 420 (i.e., the evanescently coupled light) as a function of the refractive index of the overlay 420. This relationship between the index of the overlay 420 and the optical loss in the guided light may be used for sensing. When the overlay 420 is an optical waveguide, such as a planar waveguide formed above the surface 144, the mode matching condition dictates that only certain modes can be coupled out of the fiber into the overlay waveguide 420. As indicated in FIG. 5, a change in the index of the overlay layer 420 causes a change in the evanescent coupling. At a particular value for the overlay index, the optical loss, i.e., the evanescent coupled signal, reaches a maximum. Accordingly, the remaining guided light in the fiber reaches a minimum power level under this condition.

Figure 6:
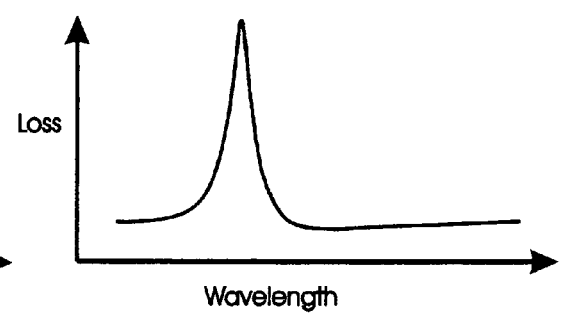

This evanescent coupling is sensitive to at least the wavelength of the guided light in the fiber. FIG. 6 shows the optical loss in such a waveguide overlay structure as a function of the wavelength of the guided light. For a fixed overlay index value, the evanescent coupling reaches a maximum at a particular wavelength. As described below, as the index of the overlay layer 420 changes, the wavelength for the maximum evanescent coupling changes and this change in wavelength may be used as one parameter to measure the change in the overlay index upon calibration. In one implementation, an optical wavemeter or an optical spectrum analyzer may be used to measure the shift in the transmission peak to determine the change in the index due to the variation in, e.g., the pressure or temperature at the location of the location of the overlay 420 and the port 144.

Figure 7A:
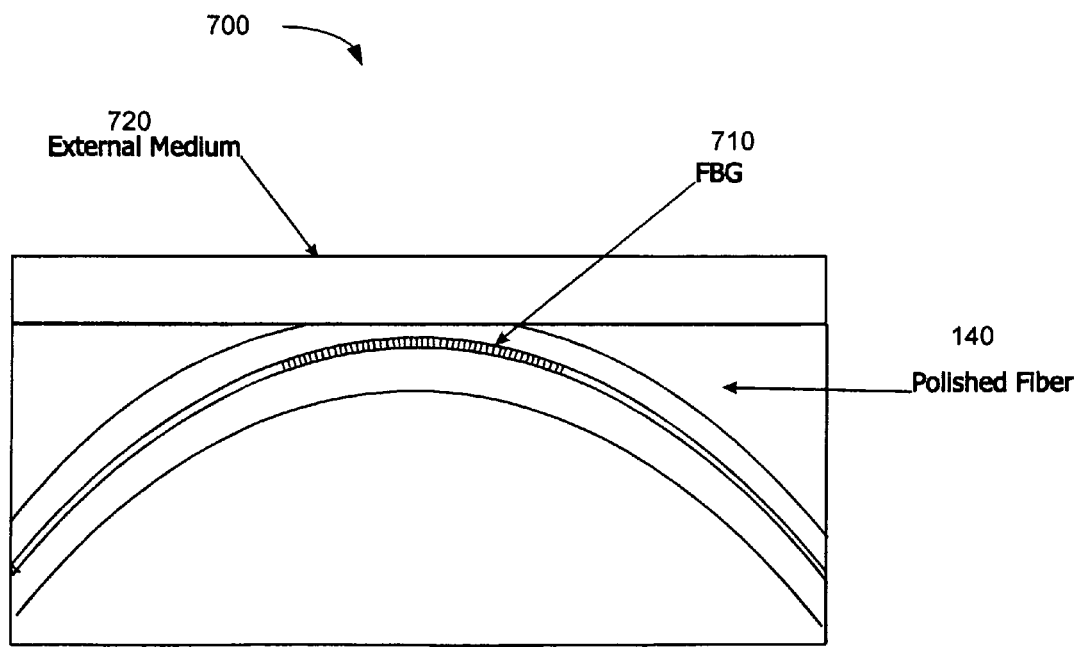
FIG. 7A shows an exemplary fiber sensing device with a fiber grating in the fiber.
Figure 7B:
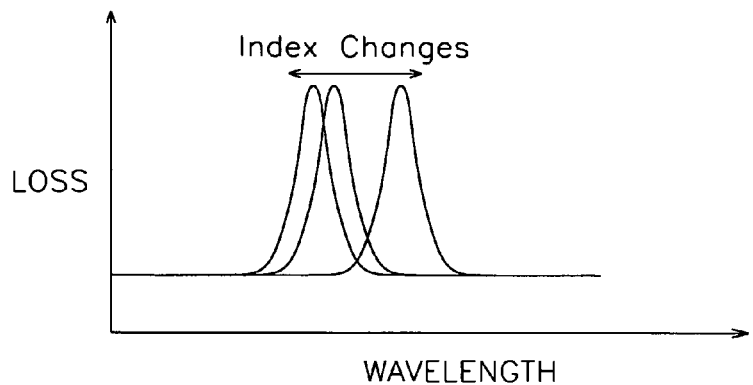
FIG. 7B shows an optical property of the device in FIG. 7B.

FIG. 7A shows a fiber device 700 where a fiber Bragg grating (FBG) 710 is formed in the fiber 140, e.g., in the fiber core, and is located at the side-polished portion. The presence of the grating 710 requires a mode matching condition on evanescent coupling. As a result, the coupling is wavelength sensitive. In addition, as the index of the external medium 720 changes, the mode matching condition changes. The grating 710 may be designed to reflect a portion of the incoming light energy of a specific wavelength back into the fiber and allow the light energy of other wavelengths to pass through. The selection of the reflection wavelength is dependent on the index of the external medium 720. Therefore, as the index of the external medium 720 changes, the reflection peak wavelength or transmission dip wavelength changes. FIG. 7B illustrates this feature by showing the shift in the transmission dip wavelength due to the variation in the index of the medium 720. This relationship, again, may be used for sensing applications where the transmitted or reflected light through the sensor in the fiber is measured to extract information such as a variation in the pressure applied to the external medium 720 or a change in temperature.

Figure 8A:
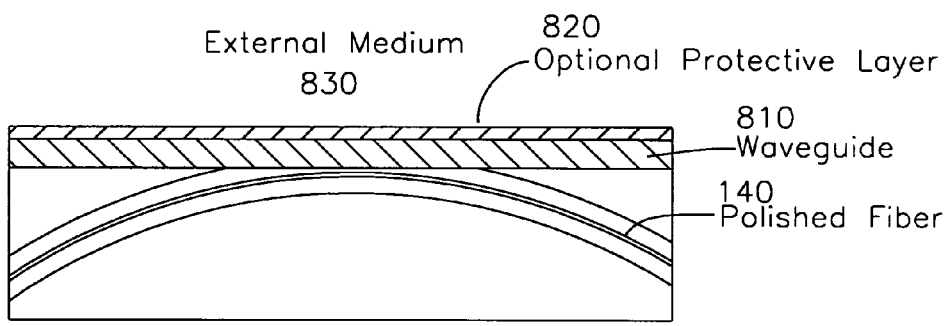
FIG. 8A shows another exemplary fiber sensing device that measures presence of selected materials.

FIG. 8A shows a fiber sensor 800 for sensing the external medium above the waveguide 810 formed over the side-polished fiber 140. A protection layer 820 may be formed on the waveguide 810 to prevent the external medium 830 under measurement from being in direct contact with the waveguide 810. This protection layer 820 should be sufficiently thin so that the layer 820 does not optically isolate the waveguide 810 from the external medium 830 and the property of the external medium 830 still affects the waveguiding operation of the waveguide 810. The optical loss at the fiber evanescent coupling port, hence, varies with the index of the external medium 830. This variation in the optical loss may be calibrated and used to measure the presence and relative volume fraction of a particular substance in the medium 830.

Figure 8B:
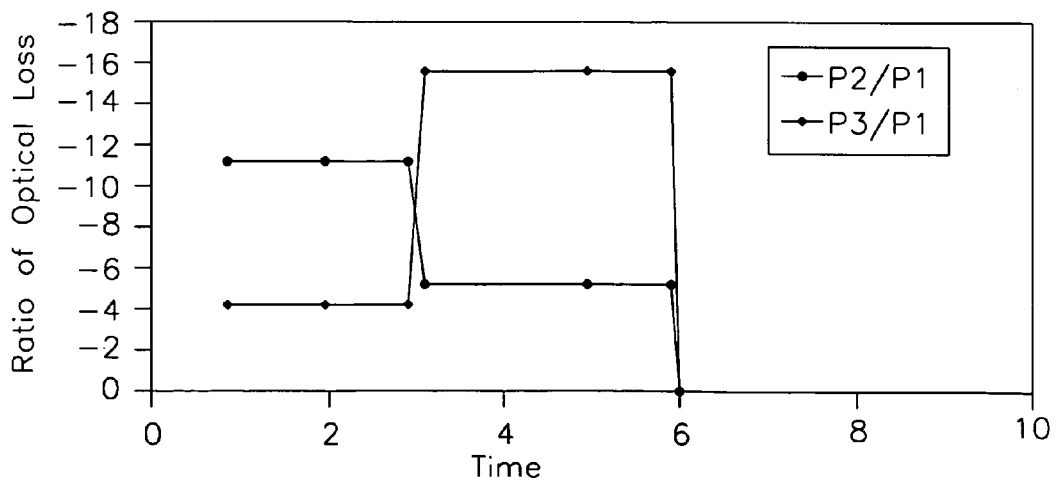
FIGS. 8B and 8C illustrate optical properties of the device in FIG. 8A.
Figure 8C:
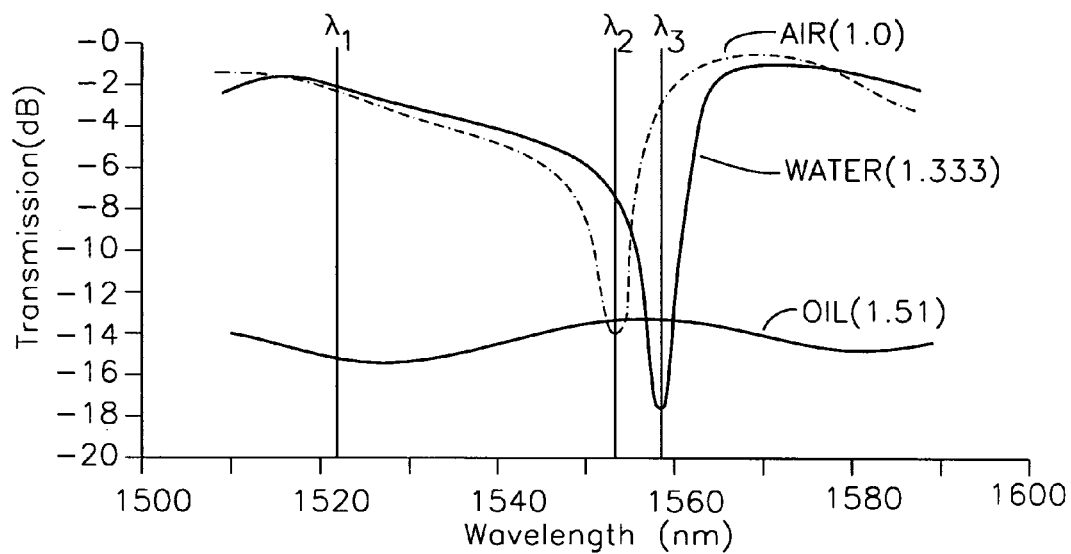

FIG. 8B shows the relative optical loss of gas, water, and oil in a mixture under measurement. The measured ratio P2/P1 is between the optical loss (P2) at the sensing port when air is present at the sensing area and the optical loss (P1) at the sensing port when oil is present at the sensing area. The optical loss P3 is the optical loss measured when water is present at the sensing area. FIG. 8C shows the transmission spectra in the fiber for the gas (air), water, and oil, respectively. The transmission spectra for the air, water, and oil are different. Air and water show prominent optical loss peaks at different wavelengths $\lambda 2$ and $\lambda 3$.

A sensing device may be configured to include multiple sensors for respectively measuring different materials. Each sensor may be configured to have a structure for sensing one particular substance and multiple such sensors designed for respectively sensing different materials may be integrated on a single substrate to form a multi-phase sensor.

Figure 9:
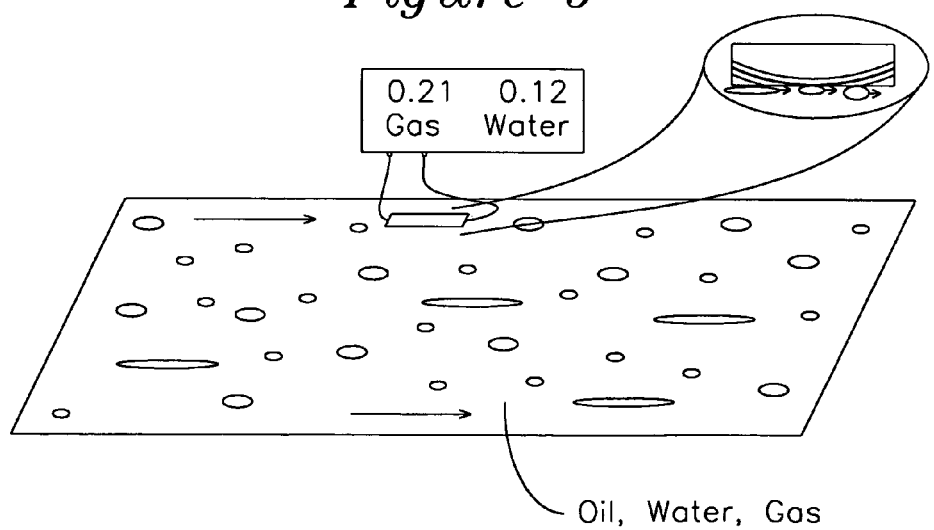
FIG. 9 shows a fiber sensing device that measures presence of water and oil.

FIG. 9 shows an example of such a 3-phase sensor that has 3 sensors for respectively detecting gas, water and oil in a mixture flow. As illustrated in FIG. 8A, the ratios of optical losses measured at the 3 different sensors may be used detect presence of air, water, and oil.

Figure 10A:
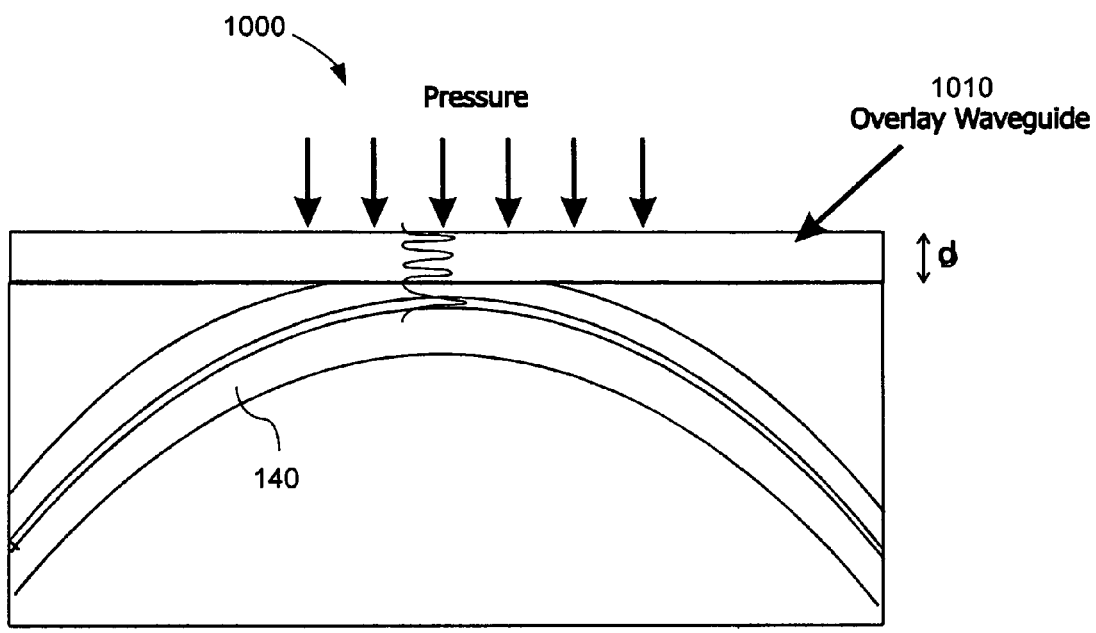
FIG. 10A shows an exemplary fiber pressure sensing device.

FIG. 10A shows an exemplary optical pressure sensor 1000. An overlay waveguide 1010 is formed over the side-polished coupling port of the fiber 140 to measure the pressure on the waveguide 1010. This device 1000 operates based on the shift in the resonance wavelength for the evanescently-coupled light caused by the pressure. The resonance wavelength can be calculated using the eigenvalue equation of the planar waveguide and fiber waveguide:

$$\lambda = \frac{2d\sqrt{n_0^2 - n_{\text{eff}}^2}}{m},$$

where the planar waveguide is a symmetric structure, $n_0$ is the index of the planar waveguide, d is the thickness of the planar waveguide, m is the mode order of the waveguide mode for the guided light, $n_{eff}$ is the effective index of the fiber mode. The free spectral range (FSR) is $$\Delta\lambda_{FSR} = \frac{2d\sqrt{n_0^2 - n_{eff}^2}}{m(m+1)}.$$

If d=20 μm, $n_{eff}$=1.447, $n_0$=1.51, m=1, then the free spectral range is 2.9 μm. The axial strain along the planar waveguide to an applied pressure P is given by $$\epsilon = -P(1-2\mu)/E,$$

where μ and E are the Poisson ratio and Young's modulus of waveguide material. The shift of the resonance wavelength to the applied pressure P is give by $$\Delta\lambda = \frac{2d(1-2\mu)\sqrt{n_0^2 - n_{eff}^2}}{mE} P = S_p P,$$

where $S_p$ is the pressure sensitivity of the sensor. The sensitivity of the sensor depends on the material properties of waveguide, waveguide thickness, waveguide index and working wavelength (defined by the mode order m). For an example, assuming $n_{eff}$=1.447, $n_0$=1.51, m=1, d=20 μm, μ=0.16, and E=0.7 Gpa, then the associated sensitivity of the sensor is calculated to be about 1 pm/psi if the waveguide material is BK7 glass. This sensitivity is higher than some other optical pressure sensors by at least one order of magnitude. Therefore, a sensitive optical pressure sensor can be constructed based on this sensing mechanism.

Figure 10B:
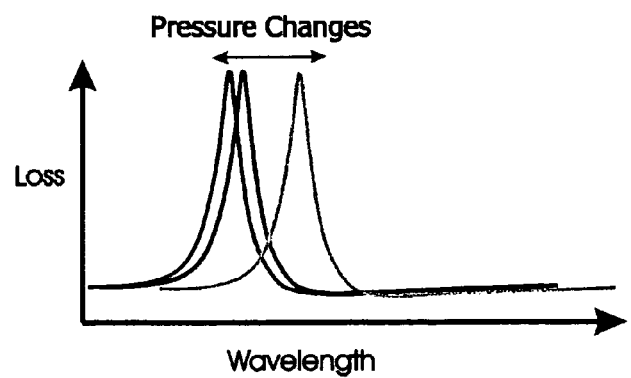
FIG. 10B shows optical properties of the device in FIG. 10A.

FIG. 10B shows the shift in the peak of the optical loss in wavelength caused by the variation in the pressure on the waveguide 1010.

FIG. 11 further shows one implementation of the above pressure sensor 1100 where a housing unit 1101 is used to package the sensor 1110 located at a location in the fiber 140. A chamber 1102 is formed in the housing to receive a flexible diaphragm 1120 upon which a pressure port 1130 is used to receive the external medium such as a liquid, gas, or a mixture of both to measure the pressure in the external medium. In this design, the external medium is in direct contact with the upper side of the diaphragm 1120 to exert the pressure to the fiber sensor via the diaphragm 1120.

In the sensor 1000 in FIG. 10A, the overlay waveguide 1010 is in direct contact with the external medium in which the external pressure is applied. Hence, the sensing operation by the sensor 1000 is affected by a change in the optical properties of the external medium, such as its index of refraction. This is undesirable in this particular application when the pressure is the parameter to be measured.

Figure 12:
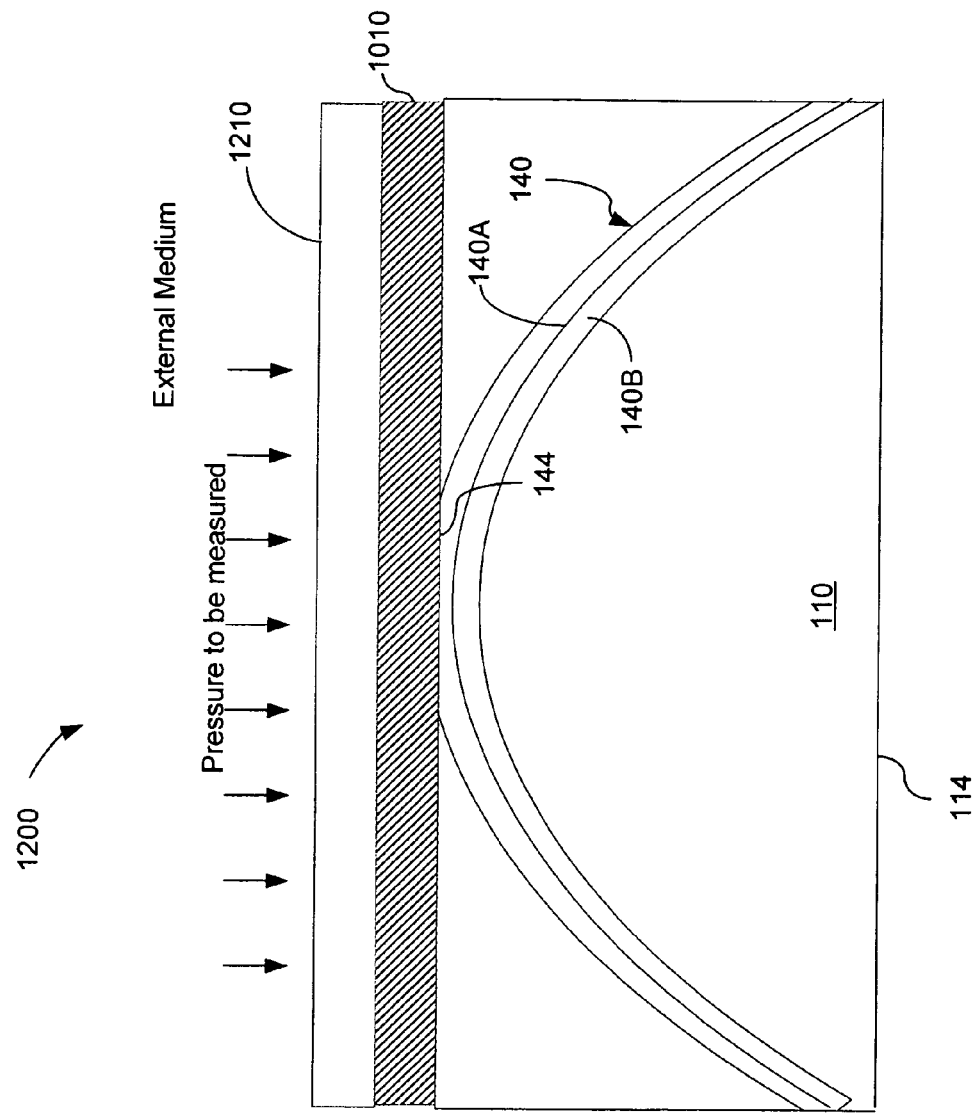
FIG. 12 shows another example of a fiber pressure sensing device.

FIG. 12 illustrates another sensor 1200 which includes an overlay layer 1210 to eliminate this effect. More specifically, an overlay layer 1210 is formed between the top surface of the waveguide 1010 and the external medium. The thickness of the overlay layer 1210 is sufficiently large that the optical field of the light coupled from the fiber 140 into the waveguide 1010 does not reach the external medium. Hence, under this condition, the layer 1210 operates as an optical insulator to optically "insulate" the waveguide 1010 from the external medium. As a result, the evanescent coupling in the sensor 1200 mainly varies with the pressure applied to the waveguide 1010 through the layer 1210.

Figure 13A:
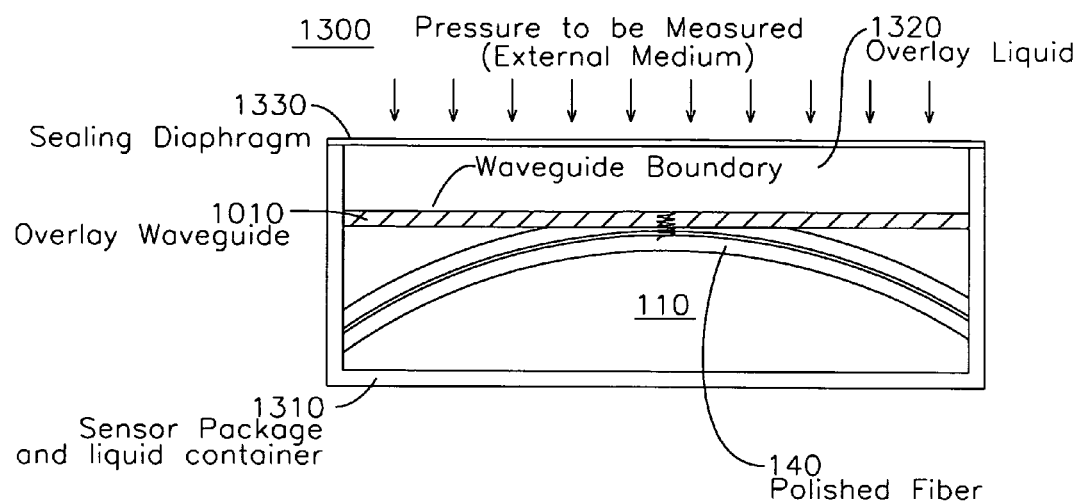
FIG. 13A shows an exemplary fiber sensing device with a waveguide overlay and a liquid overlay.

In another aspect of this application, evanescent optical coupling may be used to sense both pressure and temperature in a given environment. FIG. 13A illustrates one exemplary implementation of such a sensor 1300. An overlay liquid 1320, whose index of refraction changes in response to a pressure, is applied over and is in direct contact with the waveguide 1010. The external pressure under measurement is applied to the overlay liquid 1320. When the index of the liquid 1320 changes, the mode coupling condition at the liquid-waveguide boundary changes. This change also alters the evanescent coupling from the fiber 140 to the waveguide 1010 through the evanescent coupling port in the fiber 140. As a result, the pressure can be measured.

The sensor 1300 includes a sensor package and liquid container 1310 to hold the substrate 110 with the side-polished fiber 140 and the overlay liquid 1320. The container 1310 has an opening through which the liquid 1320 exposes to the environment where the pressure and temperature are measured. The material for the overlay liquid 1320 may be any suitable liquid or a mixture of liquids, such as water, water-based solutions, or oils. The sensor element, which includes the polished fiber 140, the waveguide overlay 1010 and the liquid overlay 1320, is placed in a sensor container package which is strong enough where no significant change in shape will occur under pressure. The waveguide 1010 may be made of suitable materials, such as semiconductors (Si, Ge, etc.), dielectric materials (glasses, SiN, SiO, etc.), or metals (Cr, Gold and others).

In operation, the external pressure under measurement is applied to the liquid 1320 to cause a change in the liquid 1320. In practice, this pressure is applied through a diaphragm 1330 on top of the liquid 1320 that seals the liquid 1320 at the opening of the container 1310. The diaphragm 1330 may be made of a thin sheet of metal such as steel, rubber or other suitable materials. The optical index of liquid 1320 can change under pressure, thus affecting the boundary condition of the overlay waveguide 1010 and also the optical coupling between fiber and waveguide 1010 through the side-polished fiber coupling port.

Figure 13B:
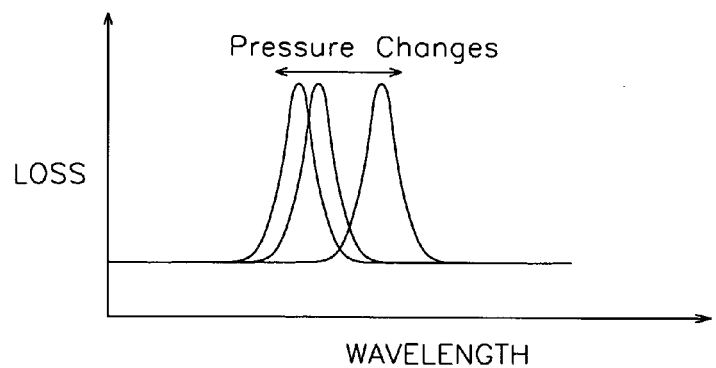
FIG. 13B illustrates the optical properties of the device in FIG. 13A.

FIG. 13B illustrates operations of the sensor 1300 in FIG. 13A by showing a shift in the resonance wavelength of the peak in the optical loss caused by the variation in pressure. Under a normal condition, the fiber 140 and waveguide 1010 have a strong coupling at a certain wavelength that satisfies the mode coupling condition (resonance condition). As the pressure changes, the strong coupling wavelength is shifted to a different resonance wavelength. By measuring the shift in the peak wavelength of the transmission dip or the peak in the optical loss, the external pressure applied to the liquid overlay 1320 can be determined.

Notably, the index of the liquid 1320 can also change with the temperature and thus, the change in the evanescent coupling can also reflect the temperature in the surrounding environment. In order to determine the pressure applied to liquid 1320, it is desirable to measure temperature precisely as well to account for the change in the coupling contributed by the change in temperature.

In designing a transmission sensor described above in FIGS. 12 and 13A, the parameters of the overlay waveguide 1010 should be designed so that the resonance condition for evanescent coupling from the fiber to the waveguide 1010 is sensitive to the change in the index of the overlay layer 1210 above the waveguide 1010. The design parameters of the waveguide 1010 include its refractive index and the thickness d. Assume that the boundary phase conditions at the interface between the side-polished fiber and the waveguide 1010 and the interface between the overlay layer 1210 and the waveguide 1010 are φ1 and φ2, respectively, the resonance condition for the evanescent coupling is $$2k_x d = 2(2\pi/\lambda)\sqrt{n_0^2 - n_{\mathit{eff}}^2}\ d = \phi 1 + \phi 2 + 2m\pi,$$

where $k_x$ is the wavevector of light along the vertical direction that is perpendicular to the fiber, $n_0$ is the refractive index of the waveguide 1010 and m is an integer. This condition is sensitive to wavelength and this wavelength dependence can be made sensitive with properly selected values for the indices of the layers 1210, 1010, and the fiber 140. For example, the boundary phase condition φ2 may be approximately an arctangent function of $$\sqrt{n_{\mathit{eff}}^2 - n_{1210}^2}\ /\ \sqrt{n_{1010}^2 - n_{\mathit{eff}}^2}\ .$$

Hence, for the case of small m such as m=3, the index of the layer 1210 ($n_{1210}$) may be designed to be near the value of the effective index $n_{\mathit{eff}}$ to obtain a strong dependence of the resonance wavelength on the pressure- or temperature-caused change of the index $n_{1210}$ of the overlay layer 1210. In particular, it is recognized that the TM mode coupling is more sensitive than the TE mode coupling. Hence, the polarization of light is controlled to be in the TM mode.

Hence, the coupling port 144 with the layers 1010 and 1210 may be configured to be sensitive to one of two orthogonal polarizations, the TM mode and TE mode. This sensitivity to the light polarization for the evanescent coupling may be advantageously used to reduce noise in the sensor 1200. In general, sensors described in this application can be designed to exhibit such sensitivity to polarization. Accordingly, an optical linear polarizer may be implemented in the sensor to substantially reduce or eliminate one polarization while maintaining light in the orthogonal polarization in the sensor.

Figure 12A:
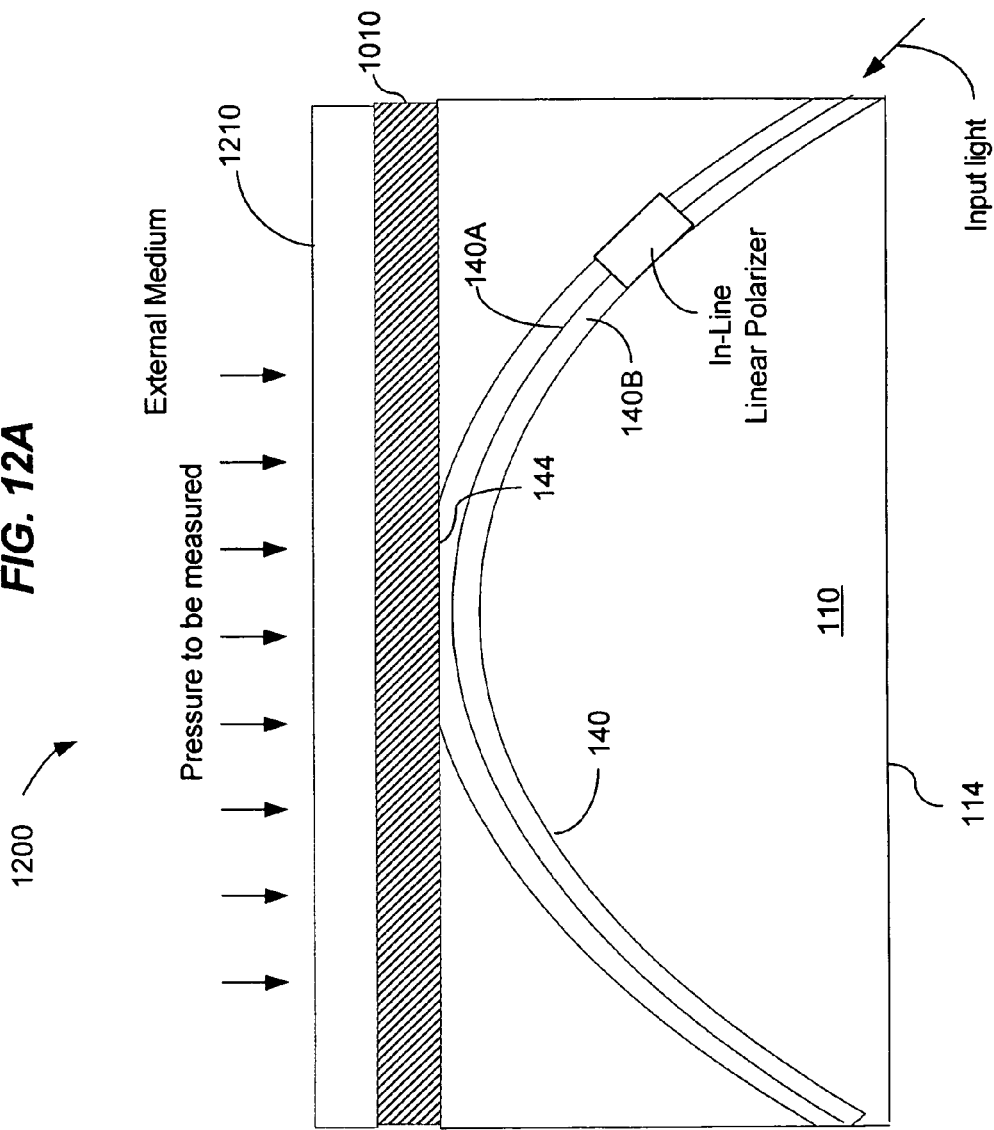

For example, in the sensor 1200 which is more sensitive to the TM mode, an in-line polarizer may be formed in the fiber 140 to control the light in the sensor 1200 to be in the TM mode by eliminating the light in the TE mode. Alternatively, a linear polarizer may be spliced to the input end of the fiber 140 to select the preferred polarization. A sensor configured to operate in the TE mode may use the in-line polarizer or a polarizer at the input end to select light in the TM mode by rejecting light in the TM mode. FIGS. 12A and 12B illustrate the sensor 1200 with an in-line linear polarizer and an input linear polarizer, respectively.

Figure 14A:
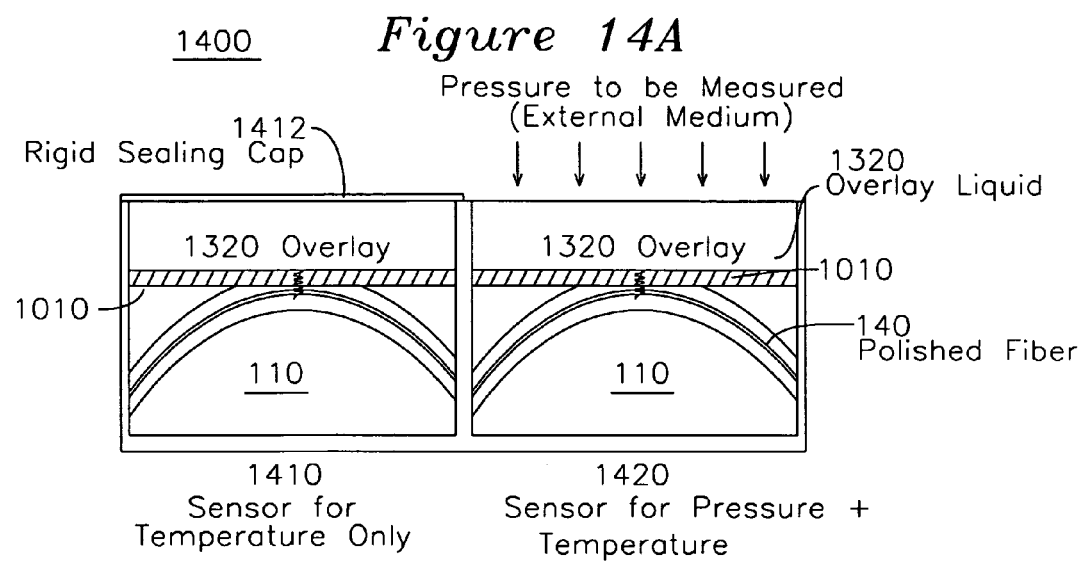
FIG. 14A shows an example of a sensing device with two fiber sensors for measurements of both temperature and pressure.
Figure 14B:
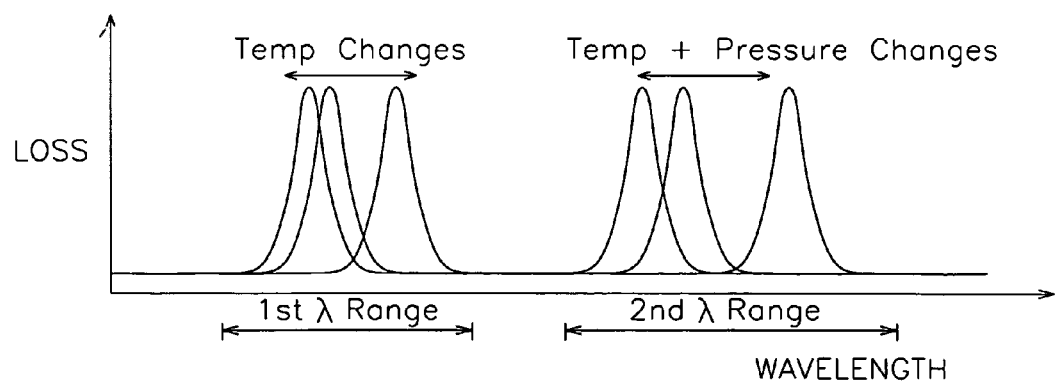
FIG. 14B shows optical properties of the two sensors in FIG. 14A.

FIG. 14A illustrates one exemplary sensor 1400 having two separate evanescent sensors 1410 and 1420 in the same fiber that are respectively used to measure temperature and pressure at the same location. The two sensors 1410 and 1420 may be built in the same way such as the design in FIG. 13A but with different resonance peak positions in wavelength as illustrated in FIG. 14B. For example, the sensor 1410 may be designed to have resonance wavelengths in a first wavelength range for its temperature sensing range while the sensor 1420 may be designed to have resonance wavelengths in a second wavelength range for its temperature and pressure ranges. The first and second resonance wavelength ranges do not overlap with each other. This feature allows for separate detection of the optical signals from the same fiber. Both sensors 1410 and 1420 are exposed to external temperatures, but only one sensor 1420 is designed to expose to the external pressure through the liquid 1320. The sensor 1410 is based on the sensor 1300 but adds a rigid sealing cap 1412 to seal off the opening so that the liquid 1320 does not receive the external pressure. The sensor 1420 is designed according to FIG. 13A to expose the liquid 1320 to the external pressure. Under this twin-sensor design, the sensor 1410 is responsive to the temperature only and can be used to calibrate out the temperature effect on the second sensor 1420. The output signals from both sensors 1410 and 1420 can be processed in a way to extract the pressure information from the signal produced by the sensor 1420. Accordingly, the sensor system 1400 in FIG. 14A can be used to obtain both temperature and pressure measurements. FIG. 14B illustrates the output transmission signals of the two sensors 1410 and 1420 during operation.

Figure 15A:
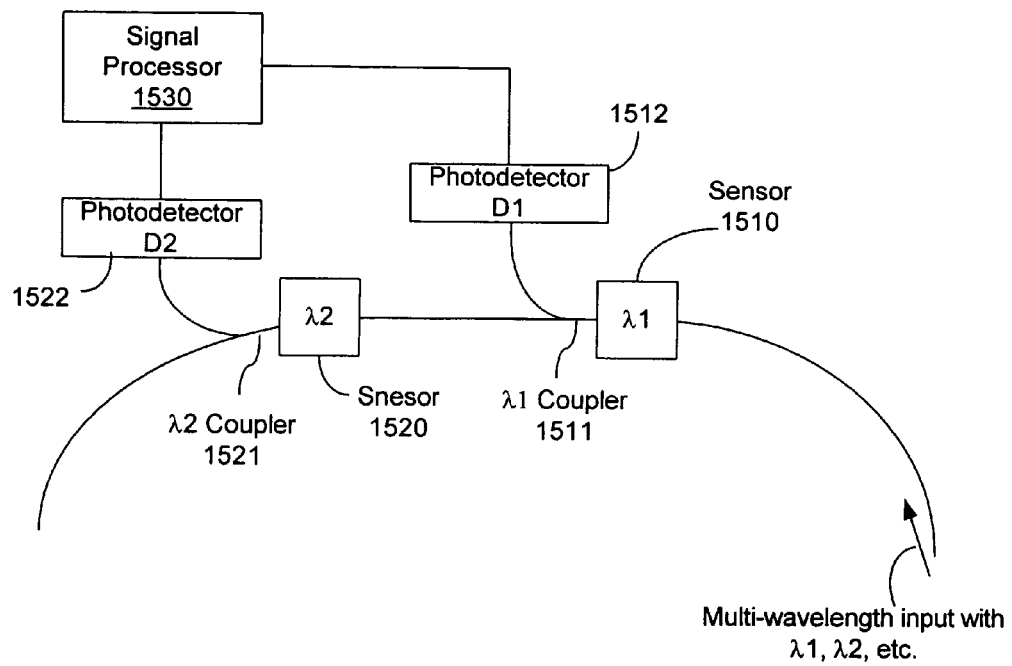
FIGS. 15A and 15B show two examples of multiple fiber sensors in a single fiber.
Figure 15B:
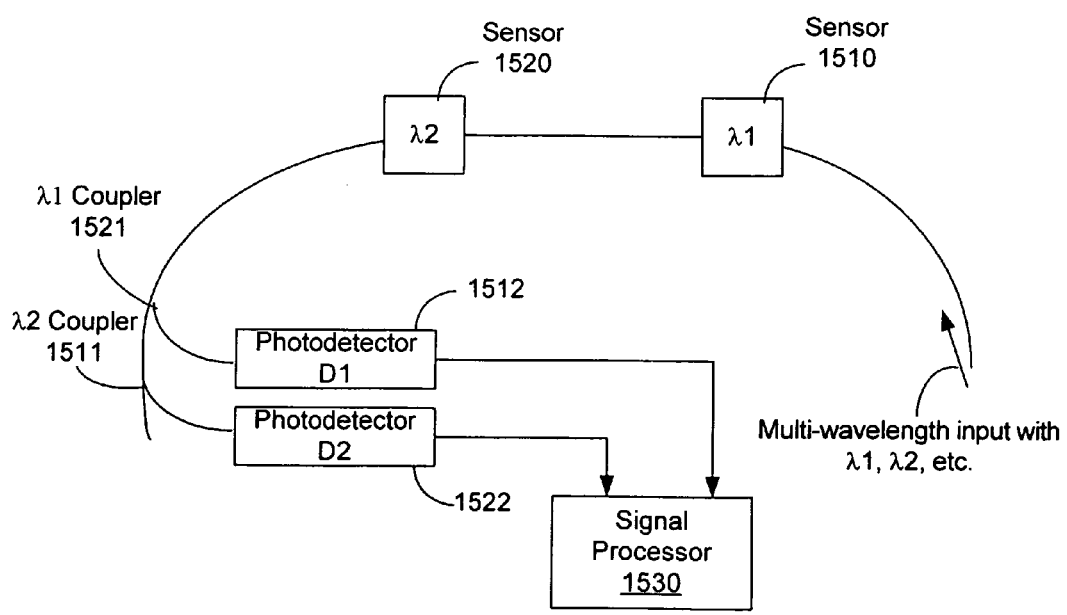

Using the above sensor designs, multiple sensors may be multiplexed to a single fiber where each sensor can work at a wavelength band different from other sensors. FIGS. 15A and 15B illustrate two examples where transmission sensors (1510, 1520, etc.) are fabricated in or coupled to a single fiber to operate at different bands with different center wavelengths λ1, λ2, etc. The sensor 1510, for example, is designed to couple and attenuate only light in the first band centered at λ1 while transmitting light in other bands, e.g., in the band centered at λ2, without attenuation.

Two different output designs may be implemented. In FIG. 15A, WDM couplers 1511 and 1521 for coupling light at different bands are locally coupled to the common fiber at the outputs of the respective sensors 1510 and 1520, respectively. Photodetectors 1512, 1522, etc. are coupled to receive the outputs of the WDM couplers 1511 and 1521, etc., respectively and are used to measure the attenuated output beams at different bands. A signal processor 1530 is coupled to receive the detector output s from the detectors 1512 and 1522 and is programmed to process the detector outputs to extract the measurements at different sensors 1510 and 1520.

Alternatively, FIG. 15B shows WDM couplers 1511, 1521, etc. for coupling light at different bands are coupled to the fiber at an output section and are spatially located away from the sensors 1510 and 1520, respectively, to output beams in different bands for measurements in detectors 1512, 1522, etc. This design separates the sensors from the detectors to allow for "remote" sensing.

In addition to the above transmission sensors, an evanescent-coupled sensor may also be designed to operate in a reflection mode. Under this reflection mode design, a reflective grating can be formed either in the fiber core or outside the fiber core within the reach of the evanescent field of the guided light so that the grating can interact with the guided light to produce a Bragg reflection. The reflective grating is designed to make the Bragg condition depend on the index of an overlay layer above the grating to sense either the pressure or temperature or both. Different from the above transmission sensors, such a reflection sensor reflects back the light in the Bragg resonance condition so that the detection is performed at the same fiber location where the input light is coupled into the fiber.

Figure 16:
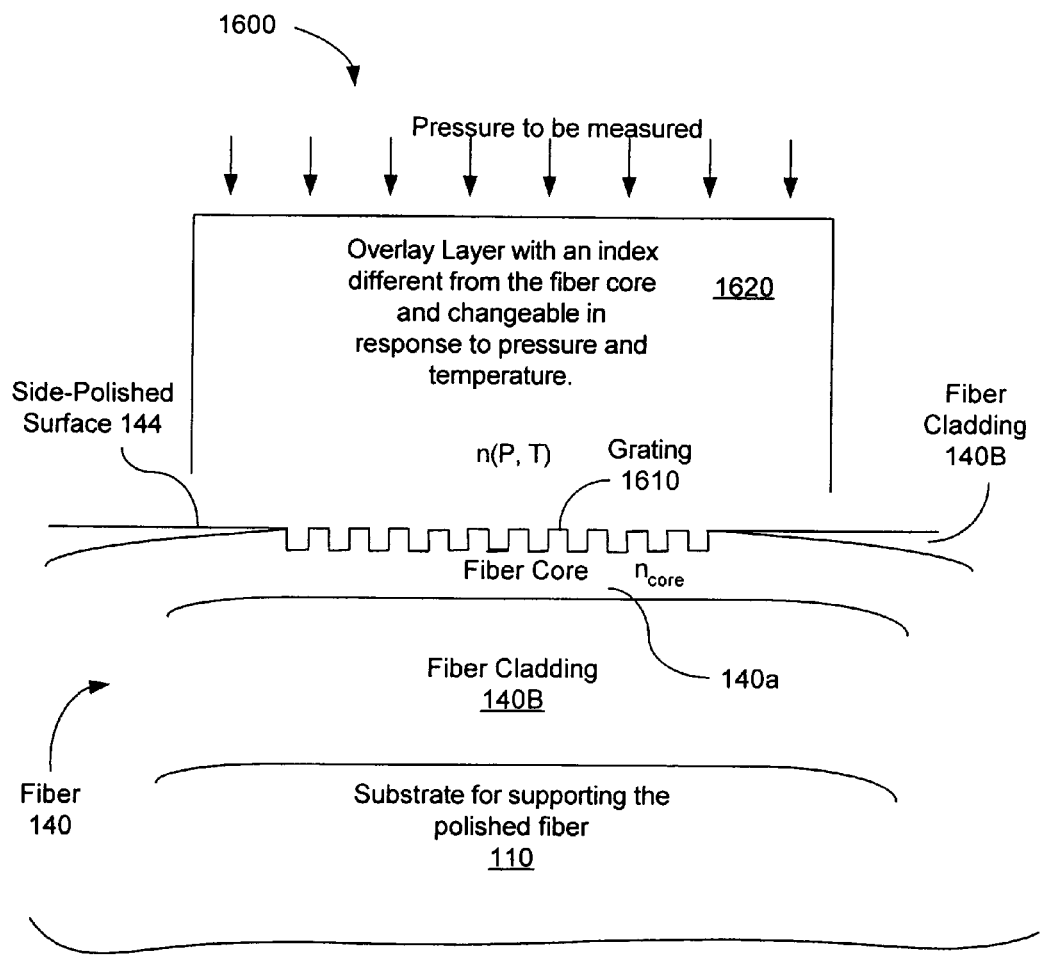
FIGS. 16 and 17 illustrate two exemplary reflective fiber sensors based on evanescent coupling.

For example, FIG. 16 shows one implementation of a reflection sensor 1600 where a reflective Bragg grating 1610 is formed in the fiber core 140A of the side-polished fiber 140 by physical grating grooves. This grating 1610 may be formed by first removing the fiber cladding to expose the fiber core and then etching grating grooves on the exposed part of the fiber core. An overlay layer 1620 with a different index n(P,T) is then filled over the grating grooves. The difference between the index of the fiber core, $n_{core}$, and n(P,T) effectuates the grating 1610. This grating 1610 is designed to have a Bragg resonance condition to couple a forward-propagating mode to a backward-propagating mode. When the index n(P,T) of the overlay layer 1620 changes, the Bragg resonance condition of the grating 1610 changes and thus the wavelength of the reflected light changes. This change in the reflected light, under proper calibration, can then be used to measure the pressure P, or temperature T that causes the change in n(P,T). In addition, when the overlay layer has an index n(P,T) lower than that of the fiber core 140A, the grating 1610 formed on the edge of the fiber core 140A may interact with only a fraction of the guided mode so the reflected signal may be insensitive to the change of index n(P,T) for certain applications.

In order to increase the sensitivity of reflected signal in response to the change of n(P,T), a thin film with index higher than that of the fiber core 140A can be added to cover the grating 1610 so as to increase the fraction of guide mode on the grating 1610. The index difference in the grating may be designed to be large to produce a strong grating coupling. This strong grating coupling may produce a broad bandwidth in the reflection peak and thus may reduce the detection spectral resolution in the wavelength domain. As a result, the measurement accuracy in the shift of wavelength of the reflection peak may be reduced.

In implementation, a high-index thin dielectric layer may be formed between the grating 1610 and the overlay layer 1620 to cover the etched grating on one side of the fiber core. This layer may have an index comparable to or greater than the index of the fiber core 140A and thus operates to increase the portion of the mode on the fiber grating so that the shift of reflection wavelength can be more sensitive to the index change in n(P,T).

Figure 17:
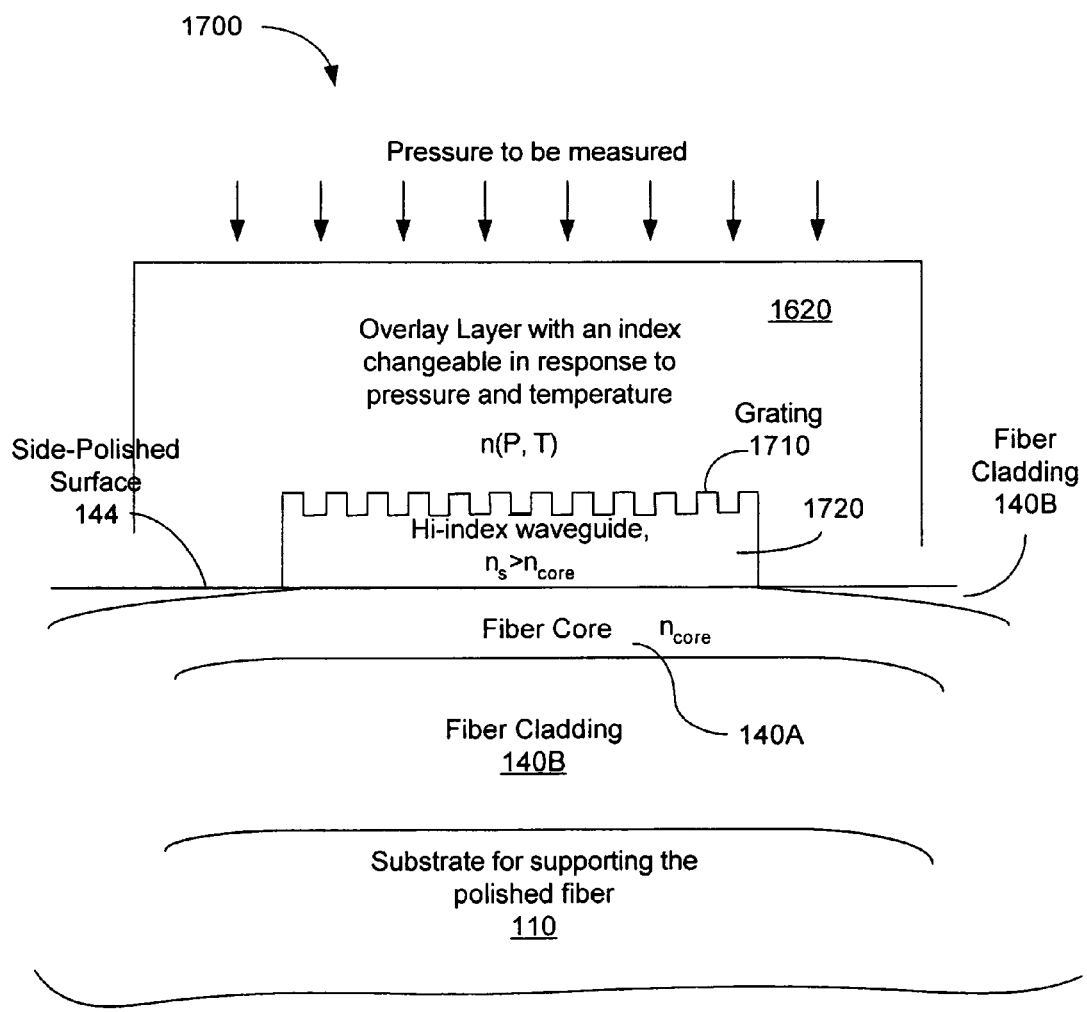

FIG. 17 shows another exemplary implementation of a reflection sensor 1700 where the reflective Bragg grating 1710 is formed outside the fiber core 140A on the top of a high-index slab or ridge waveguide 1720 over the exposed fiber core. An additional layer with index very close to that of the overlay layer 1620 is added on the top of the high-index slab/ridge waveguide 1720. The waveguide 1720 has one surface in contact with the exposed fiber core and another opposing surface processed with grating grooves (e.g., by etching). The index of the waveguide 1720, $n_g$, may be greater than the index $n_{core}$ of the fiber core 140A to shift the center of the guided mode from the center of the fiber core 140A towards the high-index waveguide 1720 so that the grating 1710 in the top surface of the waveguide 1720 can interact with a greater portion of the guided mode than the sensor 1600 in FIG. 16. On the other hand, the difference between the index of the grating layer, $n_g$, and the overlay layer 1620's index n(P,T) may be designed to be small to effectuate a weak grating coupling to achieve a narrow bandwidth in the reflection peak.

The thickness of the high-index waveguide 1720 may be small so that the grating 1710 is within the reach of the evanescent field of the guided mode in the fiber 140. In practice, the thickness of the waveguide 1720 is less than one wavelength of the guided light, usually only a fraction of the wavelength of the guided light but is sufficiently thick to support at least one guided mode. The slab/waveguide 1720 may be designed to have a desired index and thickness to allow for two different operating configurations. In the first configuration, the thickness of the slab/waveguide 1720 is sufficiently small to barely support one mode in the slab/waveguide 1720 for interaction with the grating 1710 so that the change in the index n(P,T) of the overlay layer 1620 effectively turns on or off the optical reflection caused by the grating 1710 or to change the reflected peak wavelength abruptly. In the second configuration, the thickness of the slab/waveguide 1720 is sufficiently large to support at least one mode for interaction with the grating 1710 so that there is always a grating-caused reflection signal but the strength of the reflection signal changes with the index n(P,T) of the overlay layer 1620.

In one implementation, the high-index slab/waveguide 1720 may be formed of a dielectric layer such as an aluminum oxide (AlOx) with an index around 1.75. This thickness of the slab 1720 may be approximately in the range from 80 nm to about 150 nm. The grating 1710 on top of the slab 1720 may be formed by, e.g., forming a dielectric layer such as SiOx over the slab 1720 and then etching the layer to form the grating grooves. The overlay layer 1620 over the grating 1710 with the index n(P,T) may use a variety of materials such as liquids like oil, alcohol and water. To achieve a narrow band reflection, the index of the grating material should be close to the index of the overlay layer 1620 above the grating 1710. Materials such as $SiO_2$ or similar materials whose refractive indices are close to that of the overlay layer 1620 such as 1.424 for standard oil or 1.38 for alcohol, etc. may be used to achieve a low index contrast in the grating 1710. This low index contrast of grating results in a much narrower FWHM of the reflection peak, for example, a FWHM of about 0.3 nm.

The slab 1720 over the side-polished fiber core 140A provides a physical discontinuity of the fiber 140 for guiding light confined in a guided mode. This physical discontinuity can cause the guided light to scatter and thus some optical loss. To reduce this optical loss, a transition region may be provided at the two ends of the waveguide 1720 to gradually transfer the mode initially guided by the fiber core 140A to the mode guided in the combination structure of the waveguide 1720 and the fiber core 140A.

Figure 18A:
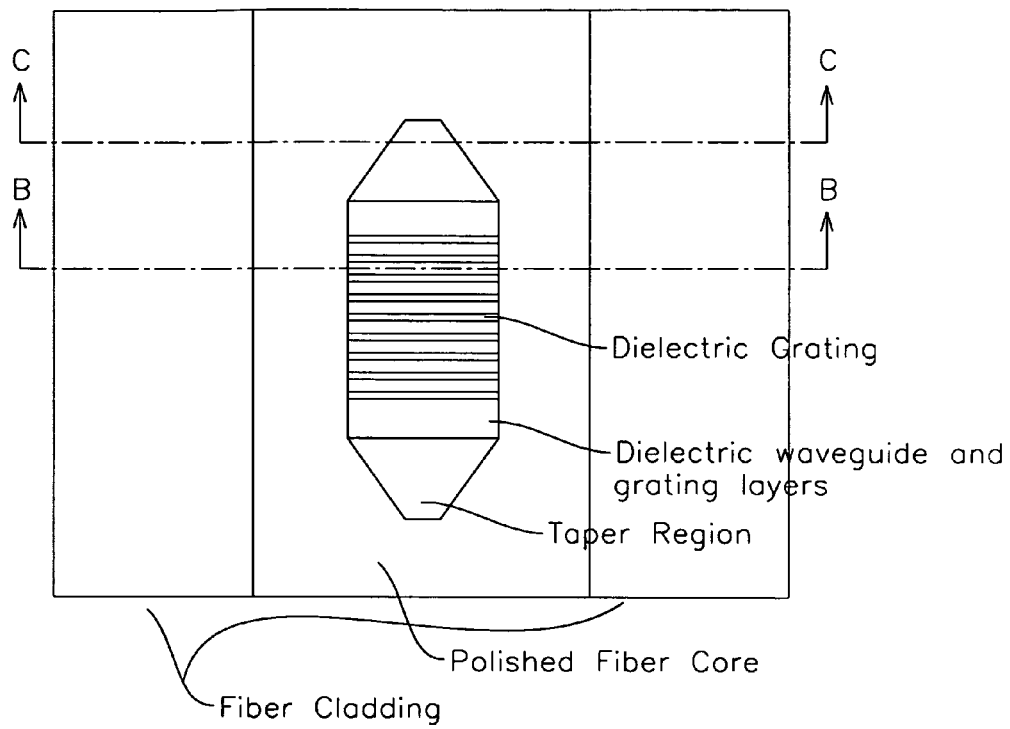
FIGS. 18A, 18B, and 18C shows one example of a waveguide formed over a polished side surface of a fiber to have a tapered transition region at each end for gradual transformation of the mode.
Figure 18B:
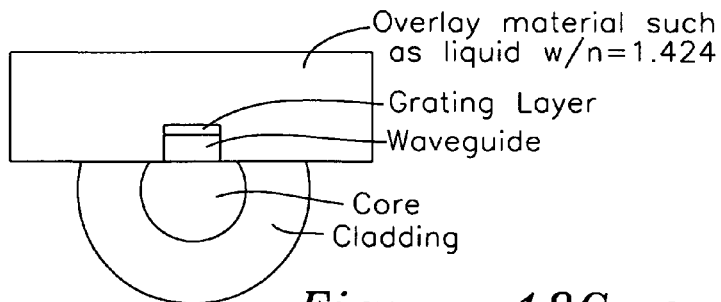
Figure 18C:
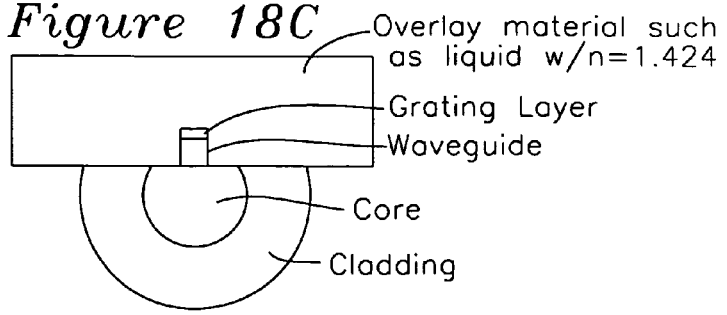

FIGS. 18A, 18B, and 18C show one implementation of a slab design with two tapered end regions. Each tapered end region gradually transforms the mode to reduce optical loss. FIG. 18A shows the top view, FIG. 18B the sectional view along the line BB, and FIG. 18C the sectional view along the line CC. The tapered end regions are designed to change their geometrical dimension in an optically gradual manner so that a guided mode can adiabatically transform without an abrupt change. An optically adiabatic change reduces the optical loss in comparison to an abrupt change that does not satisfy the adiabatic condition.

Figure 19:
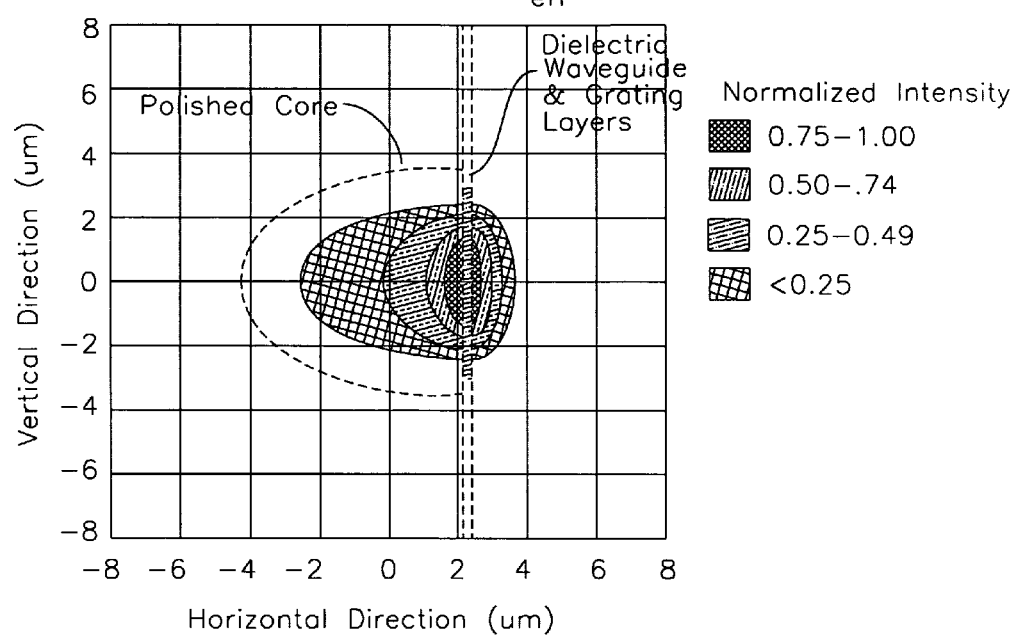
FIG. 19 shows the simulated transverse mode profile of the guided mode at the location in the waveguide shown in FIG. 17 where the guided mode is shifted away from the fiber core towards the waveguide and the grating.

FIG. 19 shows the simulated transverse mode profile of the guided mode at the location in the waveguide 1720 where the guided mode is shown to shift towards the waveguide 1720 and the grating 1710.

Figure 20:
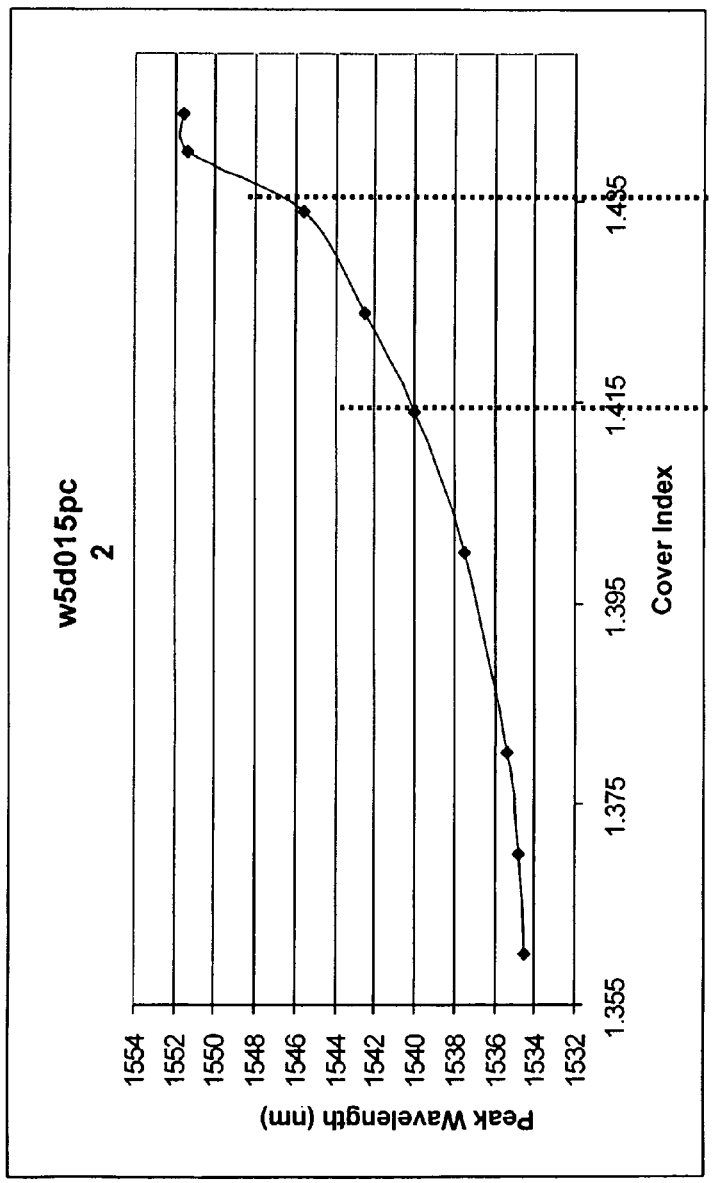
FIG. 20 shows the dependence of the wavelength of the reflection peak on the index n(P,T) of the overlay layer for sensors shown in FIGS. 16 and 17.

FIG. 20 shows the dependence of the wavelength of the reflection peak on the index n(P,T) of the overlay layer 1620. A shift of 6 nm in wavelength is illustrated for a change in the index from 1.415 to 1.435.

The reflection sensors may be used to place the optical terminal for injecting the probe light and the optical detector for receiving reflected probe light at the same location. In this aspect, the reflection sensors are different from the transmission sensors. Notably, when multiple reflection sensors are formed at different locations in a single fiber, the reflected signals from different sensors arrive at the same detection location in the fiber with different time delays. This feature may be used to distinguish signals from different sensors based on signal delays in time without relying on differences in wavelengths at different sensors as described above in the transmission sensors in a single fiber.

Figure 21:
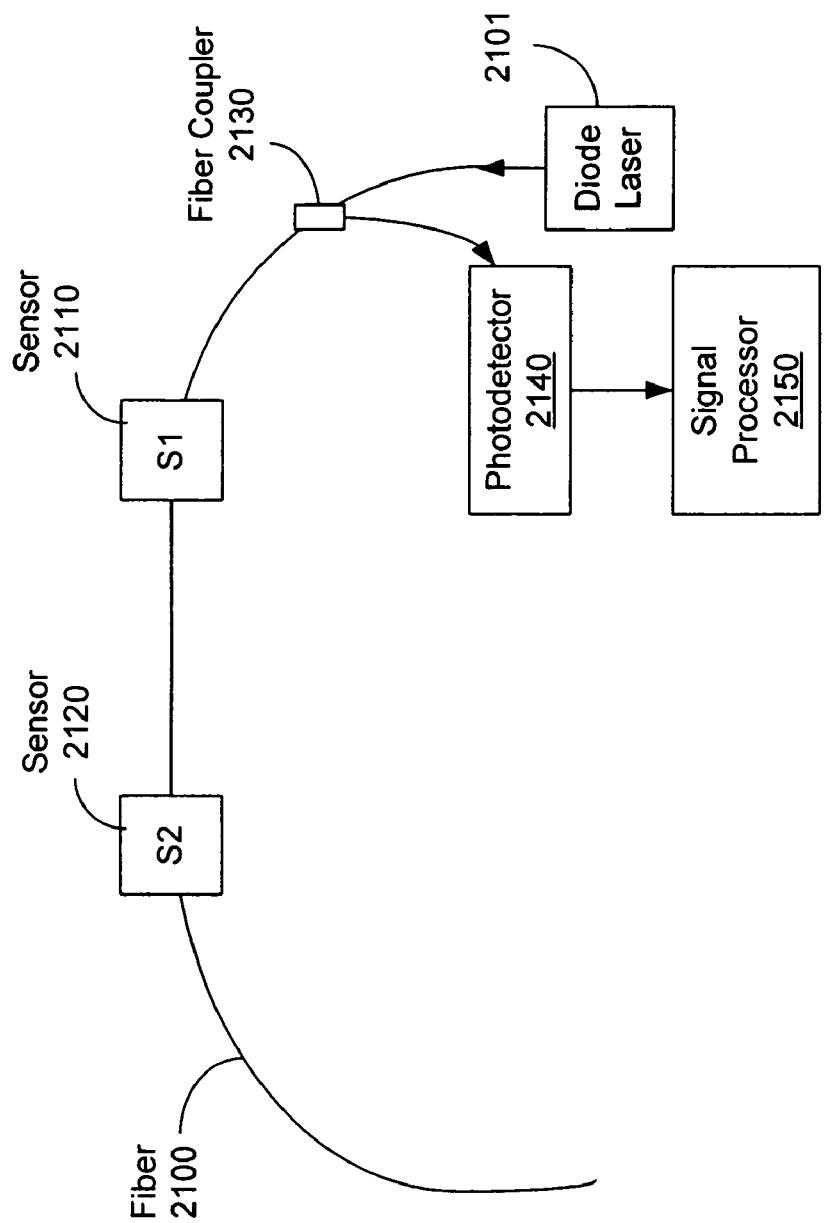
FIG. 21 shows one example of a multi-sensor system having multiple reflection fiber sensors in a single fiber.

FIG. 21 shows a fiber sensing system having at least two fiber sensors 2110 and 2120 formed at different locations in a single fiber 2100. A light source 2101 such as a diode laser is coupled to one end of the fiber 2100 to inject a probe beam into the fiber 2100. A first portion of the probe beam is reflected back at the first sensor 2110 and a second portion of the probe beam is reflected back at the second sensor 2120 at a later time. Sensors 2110 and 2120 may be configured to operate at the same wavelength. Optical reflections from different sensors propagate in the opposite direction of the original probe beam. The reflected signals may be coupled out of the fiber 2100 by using a fiber coupler or an optical circulator 2130 at a location in the fiber 2100. The optical output from the coupler or circulator 2130 is sent to an optical detector 2140. A signal processor 2150 is used to receive and process the detector output from the detector 2140 to produce the measurements at the sensors 2110 and 2120. The fiber coupler/circulator 2130, the diode laser 2101, and the optical detector 2140 may be located at the same side of the fiber 2100. The signal processor 2150 may be designed to distinguish signals from different reflection sensors based on the timings of arrival for different signals. Hence, a single optical detector 2140 may be sufficient in this multi-sensor system to measure signals from different sensors in the fiber 2100.

Only a few exemplary implementations are disclosed. However, variations and enhancements may be made.

What is claimed is:

1. A device, comprising:
   a fiber having a portion of fiber cladding and a portion of underlying fiber core removed to form a flat surface;
   a waveguide formed over said flat surface to have an index greater than said fiber core;
   grating grooves formed atop said waveguide to form a reflective Bragg grating which is within a reach of an evanescent field of guided light in said fiber to reflect guided light that satisfies a Bragg resonance condition;
   an overlay layer formed on said grating grooves whose index changes in response to an external effect; and
   a sensing unit to measure a parameter in reflected light from said grating to measure said external effect.

2. The device as in claim 1, wherein said waveguide has a thickness less than one wavelength of said guided light.

3. The device as in claim 1, wherein said waveguide has a tapered end section along said fiber to reduce an optical loss.

4. The device as in claim 1, further comprising a protection layer formed over said waveguide to prevent direct contact between the waveguide and an external medium, wherein the protection layer is thin to allow for the external medium to affect evanescent coupling at said flat surface.

5. The device as in claim 1, further comprising a housing unit which comprises:
   a chamber to hold a section of said fiber that has said grating, said waveguide, and said overlay layer, and
   a moveable diaphragm in said chamber to transmit pressure to said overlay layer in response to a pressure applied to the diaphragm.

6. A device, comprising:
   an optical fiber having a portion of optical fiber cladding and a portion of underlying optical fiber core removed to form a flat surface;
   grating grooves formed on exposed portion of said optical fiber core to form a reflective Bragg grating which is within a reach of an evanescent field of guided light in said optical fiber to reflect guided light that satisfies a Bragg resonance condition;
   an overlay layer formed on said grating grooves whose index changes in response to an external effect, said overlay layer having a tapered end section along said optical fiber to reduce an optical loss; and
   a sensing unit to measure a parameter in reflected light from said grating to measure said external effect.

7. The device as in claim 6, further comprising a thin high-index layer formed between said grating and said overlay layer.

8. The device as in claim 6, further comprising a protection layer formed over said overlay layer to prevent direct contact between the overlay layer and an external medium, wherein the protection layer is thin to allow for the external medium to affect evanescent coupling at said flat surface.

9. The device as in claim 6, further comprising a housing unit which comprises:
   a chamber to hold a section of said optical fiber that has said grating, and said overlay layer, and
   a movable diaphragm in said chamber to transmit pressure to said overlay layer in response to a pressure applied to the diaphragm.

10. A method, comprising:
   providing a fiber sensor in a fiber which comprises a side surface formed on fiber cladding, a waveguide formed over the side surface, and a reflective Bragg grating to reflect light guided by the fiber;
   exposing the fiber sensor to an external medium to cause a change at the Bragg grating;
   monitoring a wavelength shift in a spectral peak in the reflected light; and
   extracting information about the external medium based on the wavelength shift.

11. The method as in claim 10, wherein the information about the external medium includes a temperature in the external medium.

12. The method as in claim 10, wherein the information about the external medium includes a pressure in the external medium.

13. The method as in claim 10, wherein the information about the external medium includes a presence of a selected material.

* * * * *

UNITED STATES PATENT AND TRADEMARK OFFICE
CERTIFICATE OF CORRECTION

PATENT NO.       : 7,060,964 B1
APPLICATION NO.  : 10/785718
DATED            : June 13, 2006
INVENTOR(S)      : Bo Pi, Wilson Lin and Zhihao Chen It is certified that error appears in the above-identified patent and that said Letters Patent is hereby corrected as shown below:

Replace the equation on col 9 line 20 with the following equation:

$$\Delta\lambda = -\frac{2d(1-2\mu)\sqrt{n_0^2 - n_{\mathit{eff}}^2}}{mE}P = S_\rho P,$$

Signed and Sealed this

Sixth Day of January, 2009

JON W. DUDAS
*Director of the United States Patent and Trademark Office*